(12) United States Patent
Hirose et al.

(10) Patent No.: US 8,074,520 B2
(45) Date of Patent: Dec. 13, 2011

(54) ULTRASONIC INSPECTION METHOD UTILIZING RESONANT PHENOMENA

(75) Inventors: Masayuki Hirose, Tokyo (JP); Masashi Kameyama, Fukui (JP); Yukihisa Hasegawa, Fukui (JP); Nobuki Dohi, Fukui (JP); Hong Zhang, Tokyo (JP); Mitsuo Okumura, Tokyo (JP)

(73) Assignees: H & B System Co., Ltd., Tokyo (JP); The Kansai Electric Power Co., Inc., Osaka (JP); Kozo Keikaku Engineering Inc., Tokyo (JP)

( * ) Notice: Subject to any disclaimer, the term of this patent is extended or adjusted under 35 U.S.C. 154(b) by 343 days.

(21) Appl. No.: 12/299,566

(22) PCT Filed: May 12, 2006

(86) PCT No.: PCT/JP2006/309584
§ 371 (c)(1),
(2), (4) Date: May 18, 2009

(87) PCT Pub. No.: WO2007/132509
PCT Pub. Date: Nov. 22, 2007

(65) Prior Publication Data
US 2010/0024556 A1    Feb. 4, 2010

(51) Int. Cl.
*G01N 29/12* (2006.01)
(52) U.S. Cl. .......... 73/622; 73/579; 73/598; 73/602; 73/606; 73/865.8
(58) Field of Classification Search .......... 73/622, 73/623, 579, 602, 659
See application file for complete search history.

(56) References Cited

U.S. PATENT DOCUMENTS 3,916,699 A * 11/1975 Moran et al. .......... 73/623
7,600,442 B2 * 10/2009 Hirose et al. .......... 73/865.8

FOREIGN PATENT DOCUMENTS

| JP | 5-340924 A | 12/1993 |
| JP | 6-118068 A | 4/1994 |
| JP | 8-220074 A | 8/1996 |

(Continued)

OTHER PUBLICATIONS

International Search Report w/translation from PCT/JP2006/309584 dated Aug. 15, 2006 (4 pages).

(Continued)

*Primary Examiner* — Hezron E Williams
*Assistant Examiner* — Gregory J Redmann
(74) *Attorney, Agent, or Firm* — Osha • Liang LLP

(57) ABSTRACT

A transmission probe and a reception probe for transmitting and receiving a wideband ultrasonic wave are provided. Each time when the locations of the probes and are moved, a received wave $G_j(t)$ is obtained. Based on a spectrum $F_j(f)$ corresponding to the received wave $G_j(t)$, a narrowband spectrum $FA_j(f)$ is extracted. A component wave $GA_j(t)$ corresponding to the narrowband spectrum $FA_j(f)$ is found by inverse Fourier transformation. A longitudinal wave primary resonance frequency $f_1$ having a relationship with a thickness W (mm) of an inspection target and a primary resonance frequency $f_{S1}$ of a transverse wave generated by mode conversion are calculated. A comparative display of the component waves $GA_j(t)$ is presented using $f_1$, $f_{S1}$ and sizing coefficients $n_{s1}$, $n_{s2}$, $n_{s3}$ and $n_{s4}$ for high precision inspection. Based on the measurement point which shows a wave generation in the comparative screen of the component waves $GA_j(t)$, it is determined that there is a flaw Z at a certain position inside the inspection target immediately below a line segment connecting the transmission probe and the reception probe.

9 Claims, 15 Drawing Sheets

FOREIGN PATENT DOCUMENTS

WO 00/52418 A1 9/2000

OTHER PUBLICATIONS

Patent Abstracts of Japan; Publication No. 08-220074 dated Aug. 30, 1996; H&B System, Inc. (16 pages).

Patent Abstracts of Japan; Publication No. 06-118068 dated Apr. 28, 1994; Mitsubishi Heavy Industries, Ltd. (12 pages).

Patent Abstracts of Japan; Publication No. 05-340924 dated Dec. 24, 1993; Ono Sokki Co., Ltd. (15 pages).

* cited by examiner (a)

(b) A-A cross-section

ULTRASONIC INSPECTION METHOD UTILIZING RESONANT PHENOMENA

TECHNICAL FIELD

The present invention relates to an ultrasonic inspection method utilizing a resonance phenomenon for, for example, inspecting, using wideband ultrasonic waves, presence/absence of flaws inside pipes formed of stainless steel, inconel (nickel-based corrosion-resistive, heat-resistive alloy containing chromium and iron), cast iron or other metal materials, nuclear reactor pipes, turbine blades or the like or flaws in welded parts of steel structures built by, for example, construction or civil engineering works, or inspecting the size of such a flaw.

BACKGROUND ART

When a conventional ultrasonic inspection method is applied to a nuclear reactor piping system as shown in FIG. 15, the following two problems occur.

1) As shown in FIG. 15, a reactor container contains pipes of a primary piping system, and a turbine building contains pipes of a secondary piping system. As shown here, many reactor pipes are installed in both piping systems, and the total length thereof is gigantic.

The conventional ultrasonic inspection method, which is performed by repeating inspections at local sites, has a problem that a huge number of steps of the inspection work is necessary.

2) With the conventional ultrasonic inspection method, the technological determination criteria required for analysis vary depending on the person who performs measurement and analysis. Therefore, the conventional ultrasonic inspection method has a problem that an error may occur in the evaluation on the development of a tiny flaw caused by an over-time change thereof.

In order to solve the problems (1) and (2), the present applicant has already filed a patent application on an invention relating to "Ultrasonic inspection method and apparatus utilizing resonance phenomenon" (PCT/JP2004/16982).

The prior invention made by the present application relates to an ultrasonic inspection method for extracting a narrowband component wave from a wideband received wave with frequencies $n \cdot f_1$ and $n \cdot f_{s1}$ (n is an integer of 1 or greater) using resonance frequencies $f_1 = V_P/2W$ and $f_{s1} = \gamma_1 \cdot f_1$ ($\gamma_1$ is a sonic speed ratio of transverse wave and longitudinal wave).

Specifically, in order to inspect presence/absence of a flaw in a thickness immediately below a line segment connecting a pair of probes distanced by an interval of "a", which are a transmission probe and a reception probe, the following is performed. Using one method of moving the probes, the pair of probes are moved by a defined distance in a direction perpendicular to the line segment connecting the pair of probes while the interval between the pair of probes is maintained. Each time when the probes are thus moved, a wideband ultrasonic wave is input from the transmission probe and a wideband ultrasonic wave is received by the reception probe. Based on the wideband received waves $G_j(t)$ (j is the measurement point number) obtained at many measurement points, narrowband component waves $GA_j(t)$ are extracted with a sizing coefficient $n_{s4}$ at the frequencies $n \cdot f_1$ and $n \cdot f_{S1}$. A comparative display of the component waves $GA_j(t)$ is presented with the sizing coefficient $n_{s1}$, $n_{s2}$ and $n_{s3}$. Based on the generation state of the component waves $GA_j(t)$ thus displayed in comparison, the presence/absence of a flaw immediately below the line segment connecting the pair of probes is inspected for each j.

According to the prior invention made by the present applicant, the transmission probe and the reception probe are translated by a predetermined distance in a direction perpendicular to the line segment connecting the centers of the probes, so that flaws in an inspection target immediately below the line segment can be inspected all at once. Therefore, as compared with the conventional ultrasonic inspection method, the number of measurement points can be reduced to one several tenth or even to one several hundredth and thus the number of steps of the inspection work can be significantly reduced. This can contribute to the solution of the problem (1) above.

However, the above-described ultrasonic inspection method still has the following problem.

3) Due to the variety of locations and manners of movement of the probes, the method still has difficulties in terms of automatic measurement.

According to the prior invention made by the present applicant, even where different operators perform the measurements, as long as the analysis is performed with the same conditions of the sizing coefficients used for realizing higher precision of the inspection, the difference in the sizing result caused due to the varying capability of the measuring operators can be eliminated. Therefore, an accurate evaluation on the development of a tiny flaw caused by an over-time change thereof is made possible. This can contribute to the solution of the problem (2) above.

However, even with the above-described ultrasonic inspection method, there is still the following problem.

4) As a premise of the evaluation, the required received wave $G_j(t)$ needs to be obtained at exactly the same position as in the immediately previous measurement. However, due to the variety of locations and manners of movement of the probes at the time of the measurement, it is difficult to locate and move the probes in the same manner as in the immediately previous measurement.

DISCLOSURE OF THE INVENTION

Problems to be Solved by the Invention

The present invention is made in light of the problems of (1) through (4) described above. According to the conventional ultrasonic inspection method, the measurement positions are limited due to the installation state of the pipe. The present invention has an object of providing an ultrasonic inspection method utilizing a resonance phenomenon, which allows a measurement to be performed with certainty even where a flaw is present in such a position where the measurement is difficult, realizes an automatic measurement despite the variety of the locations and manners of movement of a pair of probes at the time of measurement, and can significantly reduce the measurement time even where the inspection target is a pipe having a large diameter.

Means for Solving the Problems

An ultrasonic inspection method according to the present invention is characterized in being an ultrasonic inspection method utilizing a resonance phenomenon of continuously transmitting a wideband ultrasonic wave by a transmission probe and receiving a wideband ultrasonic wave from an inspection target by a reception probe, wherein a measurement is performed with the transmission probe and the reception probe being located on a surface of a cylindrical pipe on a cross-section perpendicular to an axial direction of the pipe, where the length of a curve connecting the centers of the pair of probes is labeled as "a" and the curve is matched to an arc of the cross-section; the method comprising: executing a first step of transmitting a wideband ultrasonic wave from the transmission probe toward the central point of the cross-section of the cylindrical pipe by an externally specified number of times ($n_B$); receiving a wideband received wave by the reception probe each time when the transmission is performed; and adding the $n_B$ number of the wideband received waves $G_1(t)$ obtained in accordance with the specified number of times at a position of the receipt and averaging the addition result with a time area; executing the first step each time when the pair of probes are translated in the axial direction of the pipe by a predefined or externally given predetermined value $\Delta L$ while the pair of probes are kept as distanced by the interval "a", and executing a second step of performing the first step by an externally given predetermined number of times $n_A$ and thus obtaining all the wideband received waves $G_j(t)$ (j=1 through $n_A$); executing a third step of calculating a longitudinal primary resonant frequency $f_1$ which has a relationship with a thickness of the inspection target by:

$$f_1 = 10^6/(2W \div V_P) \quad \text{[Expression 16]}$$

where the thickness of the inspection target is W (mm), the longitudinal wave sonic speed is $V_P$ (mm/μsec) and the sonic speed ratio of a transverse wave and the longitudinal wave is $\gamma_1$, and calculating a primary resonant frequency $f_{S1}$ of the transverse wave generated by mode conversion by:

$$f_{S1} = \gamma_1 \cdot f_1, \quad \text{[Expression 17]}$$

and successively performing analyses of step 4, step 5 and step 6 shown below using sizing coefficients $n_{s1}$, $n_{s2}$, $n_{s3}$ and $n_{s4}$ for inspecting, at high precision, presence/absence of a flaw of the inspection target and time-wise development of the flaw, and using a comparative display of the obtained component waves $GA_j(t)$ to analyze the presence/absence of the flaw in the cross-section perpendicular to the axial direction of the cylindrical pipe on which the transmission probe and the reception probe are located and to analyze a position of the flaw on a circumference surface of the pipe:

step 4: step by which $G_j(t)$ is processed by Fourier transformation to find $F_j(f)$, n is an integer of 1 or greater, $f_{ST} = n \cdot f_1$ or $f_{ST} = n \cdot f_{S1}$ is found to create a frequency function $S(f)$ which has an increasing function of f=0 through $f_{ST}$, is 1.0 when f=$f_{ST}$, has a decreasing function of f=$f_{ST}$ through $2f_{ST}$ and is 0.0 when f≧$2f_{ST}$, an $FA_j(t)$ function is found by:

$$FA_j(f) = S(f)^{ns4} \cdot F_j(f) \quad \text{[Expression 8]}$$

using the sizing coefficient $n_{s4}$, and the corresponding component wave $GA_j(t)$ is found by:

$$GA_j(t) = \int_{-\infty}^{\infty} (FA_j(f) \cdot e^{i\omega t}) df \quad \text{[Expression 9]}$$

step 5: step by which a maximum amplitude of each component wave $GA_j(t)$ (j=1 through $n_A$) obtained in step 4 is found and labeled as $A_j$, the maximum value among $A_j$ is labeled as $A_{max}$, the component wave $GA_j(t)$ which fulfills $A_j \geq (1/n_{s1})A_{max}$ is replaced with $(A_{max}/A_j)GA_j(t)$, a $GA_j(t)$ wave calculated by:

$$GA_j(t) = (1/A_{max})GA_j(t) \quad \text{[Expression 6]}$$

is created, and the component wave $GA_j(t)$ is replaced with $GA_j(t)$;

step 6: step by which an $n_{s3} \cdot GA_j^{ns2}(t)$ wave is created using the sizing coefficients $n_{s2}$ and $n_{s3}$, and the $GA_j(t)$ wave is replaced with the $n_{s3} \cdot GA_j^{ns2}(t)$ wave.

According to the above-described measurement method, the measurement can be performed by sequentially moving the pair of probes only in the axial direction of the pipe while keeping the pair of probes as distanced by a predetermined interval. It is not necessary to sequentially move the probes also in a circumferential direction of the cross-section of the pipe. Therefore, especially for a pipe having a large diameter, the measurement time or the measurement work can be significantly reduced.

The inspection can be made regardless of the installation state of the pipe. Even a flaw which is made on the opposite side to the pair of probes in the circumferential direction of the cross-section of the pipe can be inspected.

Even where the pipe is covered with a protective member provided around a surface thereof, the measurement can be performed by removing the protective member only from an area where the pair of probes are to be located in the circumferential direction of the cross-section of the pipe.

Therefore, the steps of removing the protective member from all the sites to be measured and polishing the surface of the pipe after the removal can be omitted.

In addition, the above-described measurement method provides the effects that the number of the control coefficients required for an automatic measurement is significantly reduced as compared with the conventional ultrasonic method, and that the automatic control on the movement of the probes and the corresponding analysis processing are made easier.

An ultrasonic inspection method according to the present invention is characterized in being an ultrasonic inspection method utilizing a resonance phenomenon of continuously transmitting a wideband ultrasonic wave by a transmission probe and receiving a wideband ultrasonic wave from an inspection target by a reception probe, wherein a measurement is performed with the transmission probe and the reception probe being located on a surface of a cylindrical pipe on a cross-section perpendicular to an axial direction of the pipe, where the length of a line segment connecting the centers of the pair of probes is labeled as "a" and the line segment is matched to the axial direction of the cylindrical pipe; the method comprising: executing a first step of transmitting a wideband ultrasonic wave from the transmission probe toward the central point of the cross-section of the cylindrical pipe by an externally specified number of times ($n_B$); receiving a wideband received wave by the reception probe each time when the transmission is performed; and adding the $n_B$ number of the wideband received waves $G_1(t)$ obtained in accordance with the specified number of times at a position of the receipt and averaging the addition result with a time area; executing the first step each time when the line segment connecting the pair of probes is translated with respect to the axial direction of the pipe on the surface of the pipe on the cross-section perpendicular to the axis of the pipe by a predefined or externally given predetermined value $\Delta L$ while the pair of probes are kept as distanced by the interval "a"; and executing a second step of performing the first step by an externally given predetermined number of times $n_A$ and thus obtaining all the wideband received waves $G_j(t)$ (j=1 through $n_A$); executing a third step of calculating a longitudinal primary resonant frequency $f_1$ which has a relationship with a thickness of the inspection target by:

$$f_1 = 10^6/(2W \div V_P) \quad \text{[Expression 16]}$$

where the thickness of the inspection target is W (mm), the longitudinal wave sonic speed is $V_P$ (mm/µsec) and the sonic speed ratio of a transverse wave and the longitudinal wave is $\gamma_1$, and calculating a primary resonant frequency $f_{S1}$ of the transverse wave generated by mode conversion by:

$$f_{s1}=\gamma_1 \cdot f_1 \qquad \text{[Expression 17]}$$

and successively performing analyses of step 4, step 5 and step 6 shown below using sizing coefficients $n_{s1}$, $n_{s2}$, $n_{s3}$ and $n_{s4}$ for inspecting, at high precision, presence/absence of a flaw of the inspection target and time-wise development of the flaw, and using a comparative display of the obtained component waves $GA_j(t)$ to analyze the presence/absence of the flaw in a thickness in a radial direction of the cross-section of the pipe on a line extended from the line segment connecting the centers of the transmission probe and the reception probe and to analyze a position of the flaw in the axial direction of the pipe:

step 4: step by which $G_j(t)$ is processed by Fourier transformation to find $F_j(f)$, n is an integer of 1 or greater, $f_{ST}=n \cdot f_1$ or $f_{ST}=n \cdot f_{s1}$ is found to create a frequency function $S(f)$ which has an increasing function of $f=0$ through $f_{ST}$, is 1.0 when $f=f_{ST}$, has a decreasing function of $f=f_{ST}$ through $2f_{ST}$ and is 0.0 when $f \geq 2f_{ST}$, an $FA_j(t)$ function is found by:

$$FA_j(f)=S(f)^{nS4} \cdot F_j(f) \qquad \text{[Expression 8]}$$

using the sizing coefficient $n_{s4}$, and the corresponding component wave $GA_j(t)$ is found by:

$$GA_j(t) = \int_{-\infty}^{\infty} (FA_j(f) \cdot e^{i\omega t}) df \qquad \text{[Expression 9]}$$

step 5: step by which a maximum amplitude of each component wave $GA_j(t)$ (j=1 through $n_A$) obtained in step 4 is found and labeled as $A_j$, the maximum value among $A_j$ is labeled as $A_{max}$, the component wave $GA_j(t)$ which fulfills $A_j \geq (1/n_{s1})A_{max}$ is replaced with $(A_{max}/A_j)GA_j(t)$, a $GA_j(t)$ wave calculated by:

$$GA_j(t)=(1/A_{max})GA_j(t) \qquad \text{[Expression 6]}$$

is created, and the component wave $GA_j(t)$ is replaced with $GA_j(t)$;

step 6: step by which an $n_{s3} \cdot GA_j^{ns2}(t)$ wave is created using the sizing coefficients $n_{s2}$ and $n_{s3}$, and the $GA_j(t)$ wave is replaced with the $n_{s3} \cdot GA_j^{ns2}(t)$ wave.

According to the above-described measurement method, the measurement can be performed by sequentially moving the pair of probes only in the circumferential direction of the cross-section of the pipe while keeping the pair of probes as distanced by a predetermined interval.

Therefore, the measurement method according to the present invention is especially effective in the case where, for example, there is such a restriction that the pair of probes cannot be moved in the axial direction of the pipe due to the installation state of the pipe.

An ultrasonic inspection method according to the present invention is characterized in being an ultrasonic inspection method, wherein: the processing of expression 4 is executed by processing, by which $G_j(t)$ is processed by Fourier transformation to find $F_j(f)$, n is an integer of 1 or greater, $f_{ST}=n \cdot f_1$ or $f_{ST}=n \cdot f_{S1}$ is found to create a frequency function $S(f)$ which is:

0.0 when $0 \leq f < f_{ST}-\Delta f$, 1.0 when $f_{ST}-\Delta f \leq f \leq f_{ST}+\Delta f$, and 0.0 when $f_{ST}+\Delta f < f$ using a predetermined value $\Delta f$ (predefined or externally given value), and an $FA_j(f)$ function is found by:

$$FA_j(f)=S(f)^{nS4} \cdot F_j(f) \qquad \text{[Expression 8]}$$

using the sizing coefficient $n_{s4}$, and the corresponding $GA_j(t)$ wave is found by:

$$GA_j(t) = \int_{-\infty}^{\infty} (FA_j(f) \cdot e^{i\omega t}) df \qquad \text{[Expression 9]}$$

An ultrasonic inspection method according to the present invention is characterized in being an ultrasonic inspection method, comprising a step by which $\Delta f_0$ (a real number of 0 or greater) is given by an external instruction, an initial value of $f_{ST}$ is made $f_{ST} \leftarrow f_{ST}-\Delta f_0$, each time when the processing of $f_{ST} \leftarrow f_{ST}+\Delta f_{ST}$ is executed using $\Delta f_{ST}$ (a real number of 0.0 or greater which is predefined or externally instructed), the analyses of step 4, step 5 and step 6 are successively performed, a comparative display of the obtained $GA_j(t)$ waves is presented, and the analyses of step 4, step 5 and step 6 can be stopped by an external instruction.

DESCRIPTION OF THE REFERENCE NUMERALS

Figure 1:
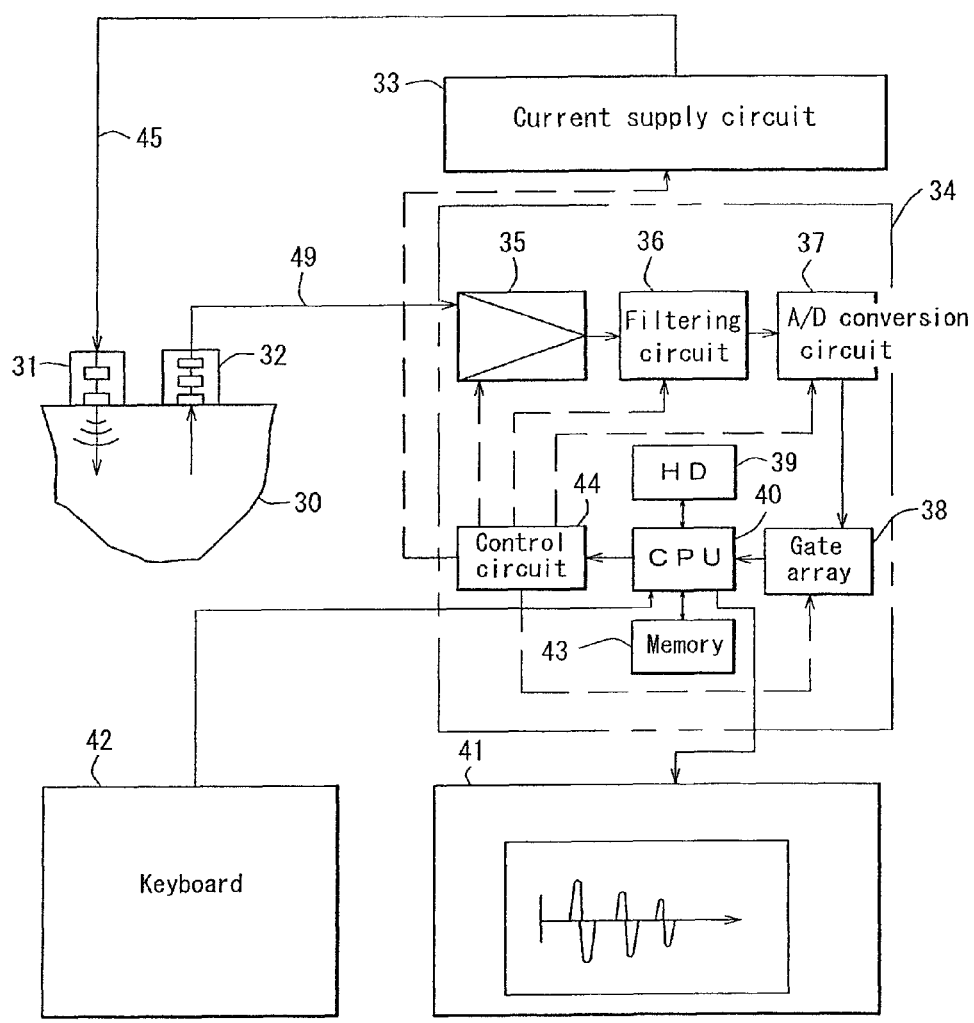
FIG. 1 is a block diagram of an ultrasonic inspection apparatus used for an ultrasonic inspection method according to the present invention.

30 Inspection target
31 Transmission probe
32 Reception probe
40 CPU (inverse transformation section)
41 Display device (comparative display section, determination section)
47 Oscillator Z Flaw
Y Protective member

BEST MODE FOR CARRYING OUT THE INVENTION

Hereinafter, one embodiment of the present invention will be described with reference to the drawings.

The drawings show an ultrasonic inspection method and an apparatus used therefor. First, with reference to FIG. 1, an ultrasonic inspection apparatus used for the method will be described.

A transmission probe 31 and a reception probe 32 are provided in contact with a surface of an inspection target 30.

The transmission probe 31 is for transmitting a wideband ultrasonic wave (e.g., 0 to 2.0 MHz), and the reception probe 32 is for receiving a wideband ultrasonic wave.

The transmission probe 31 is supplied with an electric current from a current supply circuit 33 in an ultrasonic transmission device. From the transmission probe 31, an ultrasonic wave is transmitted and enters the inspection target 30.

The ultrasonic wave signal received by the reception probe 32 is input to an analysis device 34 and analyzed.

In the analysis device 34, the signal received by the reception probe 32 is amplified by an amplification circuit 35, then filtered by a filtering circuit 36, converted into a digital signal by an A/D conversion circuit (analog/digital conversion circuit) 37, and input to a CPU 40 via a gate array 38.

On a hard disc 39, analysis processing application software, and time series data processed by a computation by the CPU 40, are stored. The CPU 40 is an inverse transformation section for finding a component wave $GA_j(t)$ described later by Fourier transformation.

The result of the above-mentioned analysis is also input to a display device 41 to be displayed. The display device 41 is a comparative display section which is used for display of a narrowband spectrum $FA_j(f)$ and comparative display of the component wave $GA_j(t)$ described later.

The ultrasonic inspection apparatus is further structured such that necessary information is input from a keyboard 42 as input means to the CPU 40. A memory 43 is used for temporarily storing data when the CPU 40 performs a computation. The CPU 40 outputs a control signal to a control circuit 44, and the control circuit 44 outputs an activation instruction signal to the amplification circuit 35, the filtering circuit 36, the A/D conversion circuit 37, the gate array 38 and the current supply circuit 33.

Figure 2:
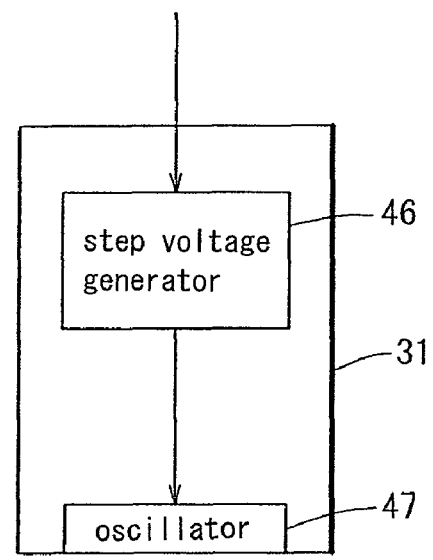
FIG. 2 is a block diagram of a transmission probe.

The current supply circuit 33 is connected to the transmission probe 31 via a coaxial cable 45. As shown in FIG. 2, a step voltage generator 46 in the form of a substrate and an oscillator 47 having a diameter φ of 10 mm are built in the transmission probe 31.

Figure 3:
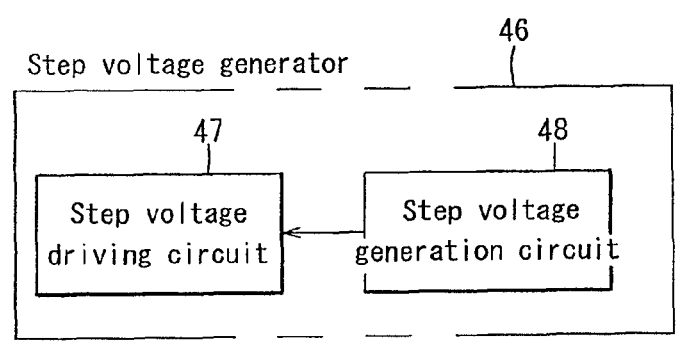
FIG. 3 is a block diagram of a step voltage generator.

As shown in FIG. 3, the step voltage generator 46 includes a step voltage driving circuit 53 and a step voltage generation circuit 48. A step function type voltage generated by the step voltage driving circuit 53 is applied to the oscillator 47.

Each time when a wideband ultrasonic wave is input to the inspection target 30, a received wave is obtained by the reception probe 32.

The received wave is transmitted to the amplification circuit 35 in the analysis device 34 via a coaxial cable 49 as time-wise change data of voltage. The time-wise change data of voltage which is transmitted to the amplification circuit 35 reaches the A/D conversion circuit 37 via the filtering circuit 36. An analog amount of this voltage is converted into a digital amount by the A/D conversion circuit 37 and transferred to the CPU 40 via the gate array 38. Thus, a time history of the digital value of voltage is displayed on the display device 41.

An instruction on voltage amplification or damping and on low or high pass filtering is conveyed to the CPU 40 automatically or by an external instruction given using the keyboard 42. The CPU 40 controls the amplification circuit 35 and the filtering circuit 36 via the control circuit 44.

Figure 4:
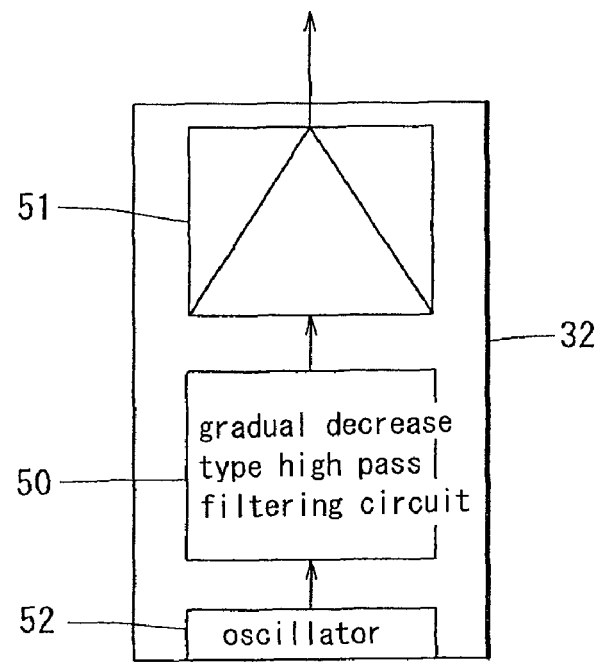
FIG. 4 is a block diagram of a reception probe.

As shown in FIG. 4, a gradual decrease type high pass filtering circuit 50 having a cut-off frequency gradually decreasing in the range of 100 kHz to 300 kHz, an amplification circuit 51, and an oscillator 52 having a diameter φ of 10 mm are built in the reception probe 32.

The current supply circuit 33 is controlled by the control circuit 44 to operate at a predetermined time interval.

Accordingly, an ultrasonic wave enters the inspection target 30 from the oscillator 47 (see FIG. 2) built in the transmission probe 31 at a predetermined time interval.

Each time when an ultrasonic wave is input to the oscillator 52 (FIG. 4) built in the reception probe 32, the oscillator 52 is excited in accordance with a change in the sound pressure of the inspection target 30. A time-wise change of the voltage which occurs in the oscillator 52 by the excitation is subjected to primary processing by the filtering circuit 50 and the amplification circuit 51 in the reception probe 32.

On the stage where the control on the amplification circuit 35 and the filtering circuit 36 in FIG. 1 is finished, the control circuit 44 is operated by an instruction from the CPU 40 to instruct the gate array 38 to add the received waves.

The gate array 38 performs addition of a time history digital amount regarding the voltage obtained by the A/D conversion circuit 37 by a specified number of times each time when the time history is obtained. Under the control of the CPU 40, the gate array 38 creates an addition average time history and displays the time history on the display device 41 at real time.

The filtering circuit 50 and the amplification circuit 51 are built in the reception probe 32, and the filtering circuit 36 and the amplification circuit 35 are built in the analysis device 34. The high pass filtering circuit 50 and the amplification circuit 51 built in the reception probe 32 are for performing primary processing on a received wave. The amplification circuit 35 and the filtering circuit 36 built in the analysis device 34 are for performing fine adjustment on the received wave, which has been subjected to the primary processing, under the control of the CPU 40. Since the fine adjustment is performed in order to improve the functions of the apparatus, the amplification circuit 35 and the filtering circuit 36 may be omitted.

Now, with reference to FIGS. 5(a) and (b), a pipe model which is to be the inspection target 30 of the measurement performed by the ultrasonic inspection method in this embodiment will be described.

Figure 5:
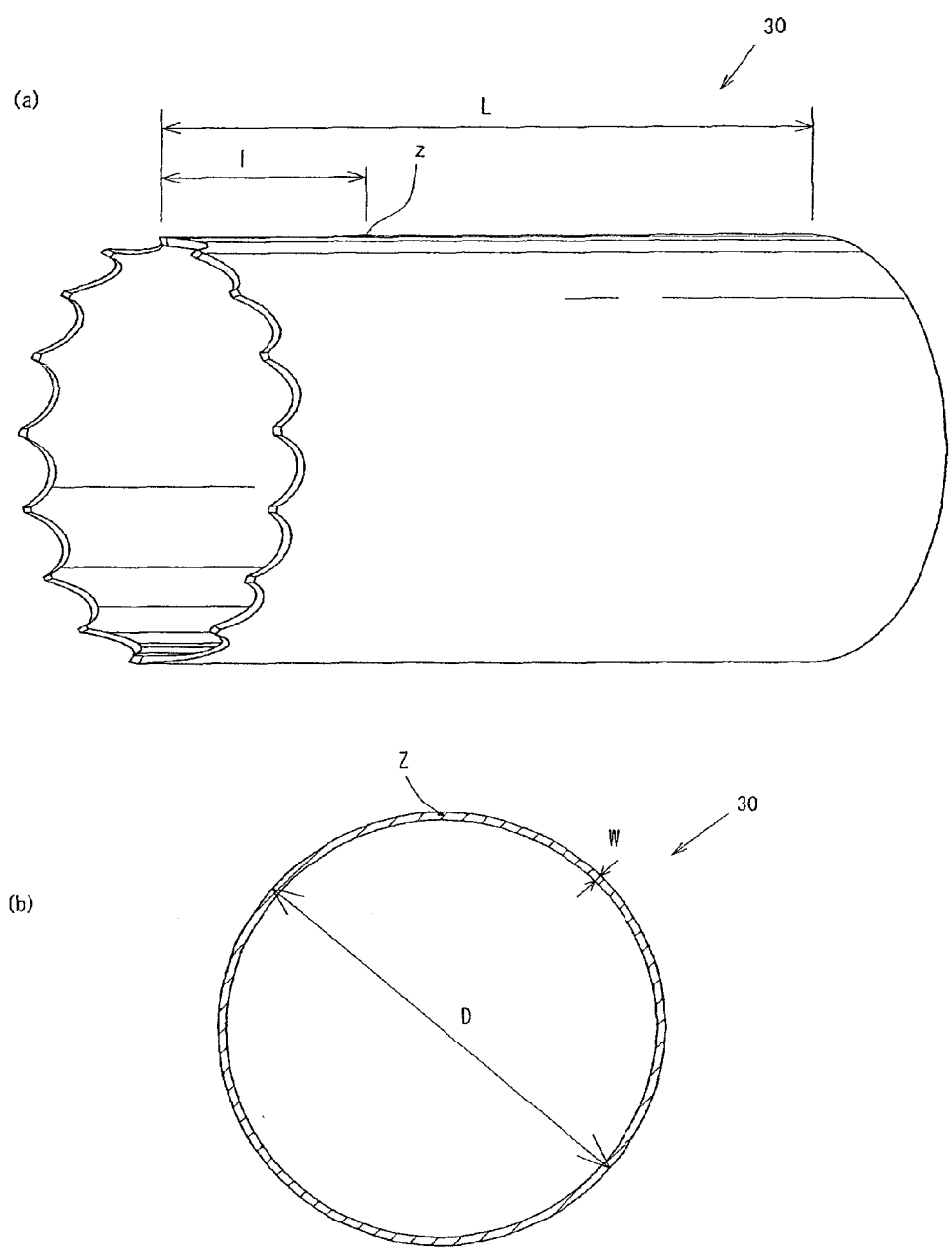
FIG. 5 shows illustrations of a pipe model.

FIG. 5(a) is an external view of the pipe, and FIG. 5(b) is a cross-sectional view thereof taken at the position of a flaw in an axial direction of the pipe.

The pipe model is an SUS pipe model and has an outer diameter D of 557 mm, a length L of 1000 mm and a thickness W of 11 mm. A tiny pseudo flaw Z extending in the axial direction of the pipe and having a length of 20 mm, a width of 0.2 mm and a depth of 1.6 mm is made at a position which is away from one end of the pipe by a distance l of 250 mm.

On such a pipe model, the transmission probe 31 and the reception probe 32 are set. As shown in FIGS. 6(a) and (b), the transmission probe 31 and the reception probe 32 are located on a circumferential surface of a cross-section of the pipe which is perpendicular to the axis of the pipe. A distance $a_1$ between the pair of probes along the longer arc of the circumference is $a_1$=1500 mm, and a distance $a_2$ between the pair of probes along the shorter arc of the circumference is $a_2$=250 mm.

As shown in FIG. 6(a), the pair of probes 31 and 32 are moved in the direction of arrow C while the interval therebetween is maintained at $a_2$. Each time when the pair of probes 31 and 32 are moved by ΔL of 5 mm, a wideband ultrasonic wave is transmitted $n_B$ times successively from the transmission probe 31 toward the center of the cross-section perpendicular to the axis of the pipe. Each time when the wideband ultrasonic wave is transmitted, a wideband received wave $G_{jk}(t)$ (j=1 through $n_A$, j is the measurement point number; k is any one value of 1 through $n_B$) is obtained. After the successive transmission is finished, the wideband received wave to be used for the analysis is evaluated by expression 1.

$$G_j(t) = \frac{1}{n_B} \sum_{k=1}^{nB} G_{jk}(t) \qquad \text{[Expression 1]}$$

Figure 7:
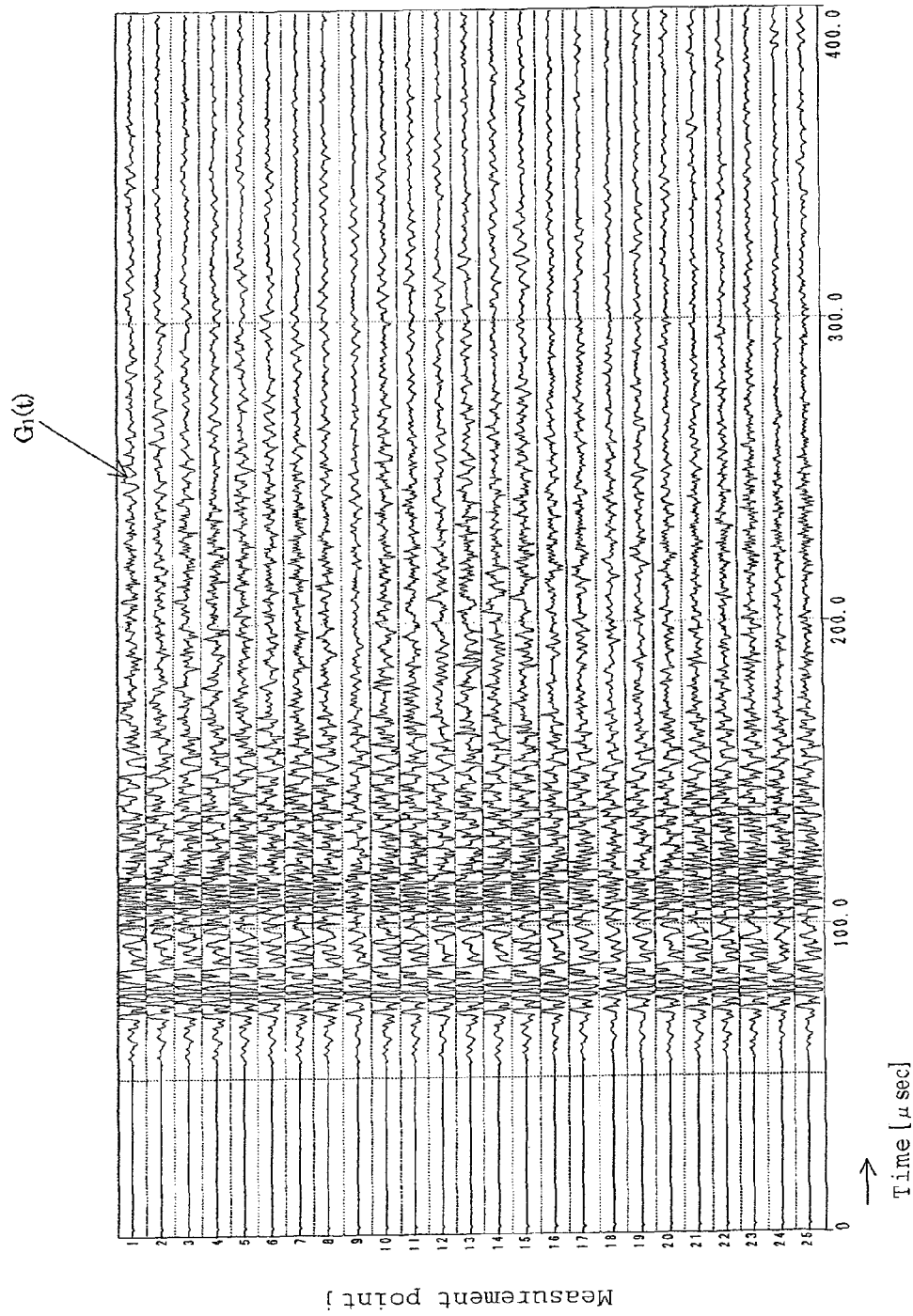
FIG. 7 is a chart comparing the receivedwaves $G_j(t)$ at different measurement points.

FIG. 7 shows waveforms of the received waves $G_j(t)$ (j=1 through 25) for comparison.

Figure 6:
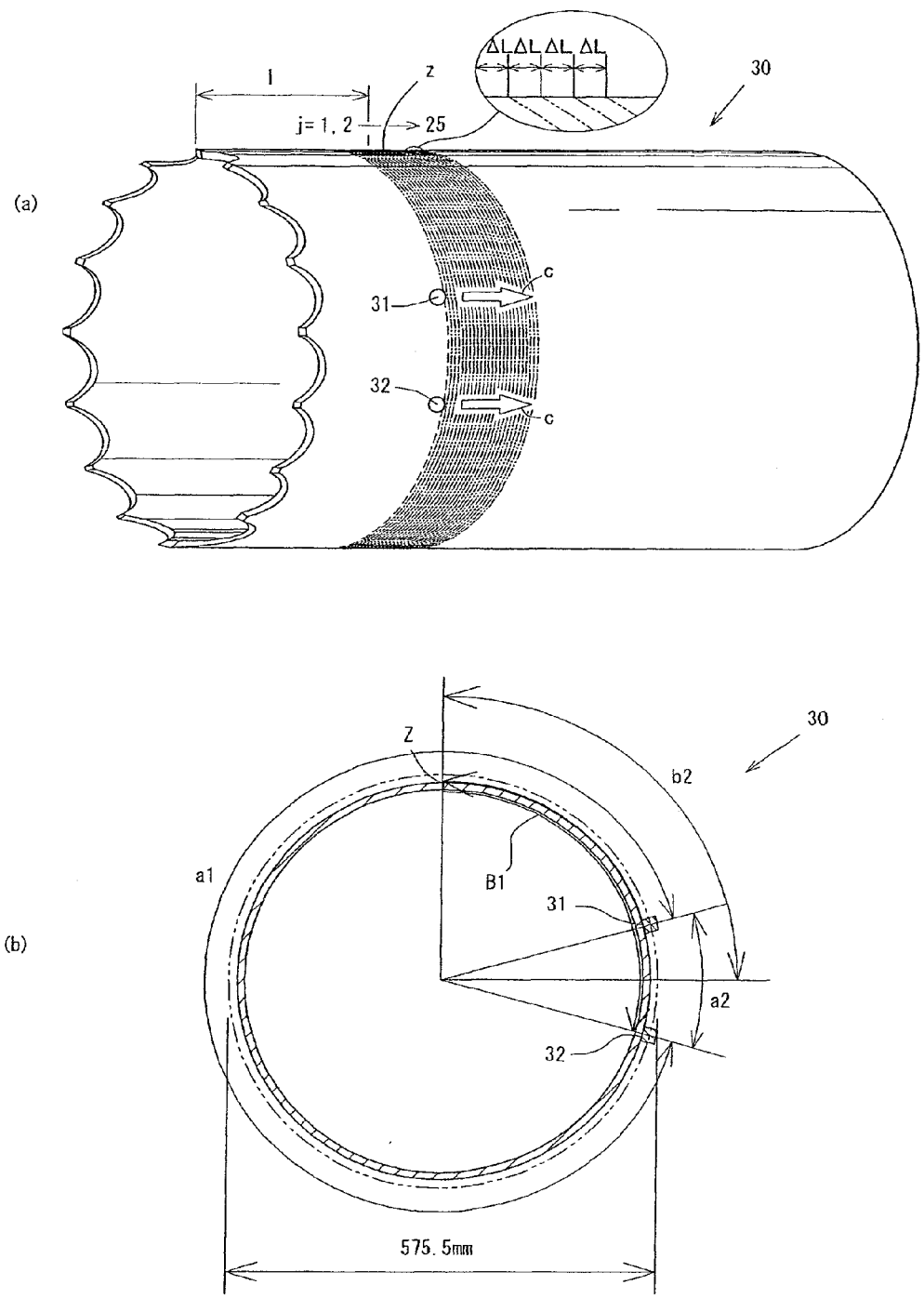
FIG. 6 shows illustrations of a measurement by which the probes provided at a set positions are moved in an axial direction of the pipe.

FIG. 6 shows the positional relationship between the flaw and the pair of probes 31 and 32. Based on this, the received wave $G_j(t)$ is obtained by the measurement, in which a length $b_2$ on the arc between the position of the flaw and the position of the center of a line segment connecting the transmission probe 31 and the reception probe 32 is:

$$b_2 = \pi \times 557.55 \text{ mm}/4 = 437.5 \text{ mm} \qquad \text{[Expression 2]}$$

Since the position of the flaw is as close as 250 mm from the end of the pipe, it is expected that the received wave $G_j(t)$ contains a great amount of wave reflected by the end of the pipe. In the case of inspecting presence/absence of a flaw Z as in this measurement, such a wave reflected by the end of the pipe is an inspection disturbing wave having a large amplitude.

Figure 8:
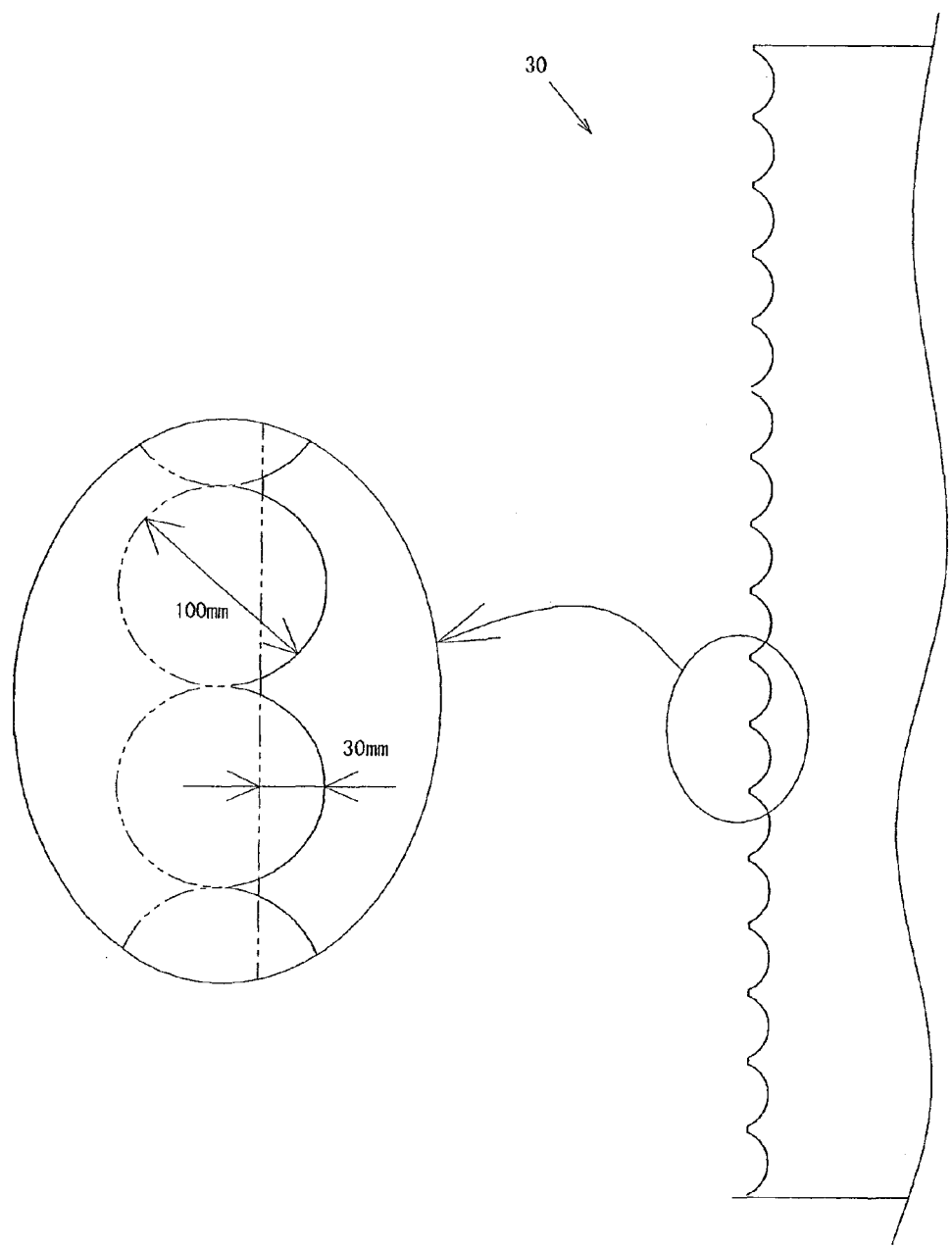
FIG. 8 illustrates an end of the pipe in an enlarged view.

Therefore, as in FIG. 8 which shows the end of the pipe in an enlarged view, the received wave $G_j(t)$ is found after the end of the pipe is continuously cut out with an arc having a diameter of 100 mm, so that the inspection disturbing wave generated at the end of the pipe is scattered.

Now, relational expressions used for the ultrasonic inspection method in this embodiment will be described.

As described above, the wideband received wave obtained by inputting a wideband longitudinal ultrasonic wave toward the center of the cross-section of the pipe from the surface of the pipe is labeled as $G_j(t)$. A spectrum $F_j(f)$ of the wave of each j of the receive wave $G_j(t)$ is formed of a group of resonance spectra (having an order) having a relationship with the thickness of the pipe.

The frequency of this spectrum has an order. Where the longitudinal wave sonic speed of the pipe material is $V_P$ mm/μsec, each resonant frequency of the longitudinal wave spectrum is represented by expression 3.

$$f_1 = 10^6/(2W \div V_P) \qquad \text{[Expression 3]}$$
$$f_2 = 2f_1$$
$$f_3 = 3f_1$$
$$\vdots$$
$$f_{nc} = n_c \cdot f_1$$

On the other hand, some of the transverse waves naturally occurring in the inspection target after the longitudinal wave is input have a resonance frequency represented by expression 4. In should be noted that the transverse wave sonic speed of the pipe material is $V_S$ mm/μsec.

$$f_{s1} = \gamma_1 \cdot f_1 = 10^6/(2W \div V_s) \qquad \text{[Expression 4]}$$
$$f_{s2} = 2f_{s1}$$
$$f_{s3} = 3f_{s1}$$
$$\vdots$$
$$f_{snc} = n_c \cdot f_{s1}$$

The wideband ultrasonic wave which is input to the pipe by the transmission probe 31 is a longitudinal wave directed toward the center of the cross-section of the pipe from the surface of the pipe. Therefore, it is natural that the received wave contains a spectrum component regarding the longitudinal waves having the resonance frequencies represented by expression 3. However, the received wave also contains a spectrum component having the resonance frequencies represented by expression 4 (transverse waves). The reason for this is that there is a physical phenomenon called mode conversion of an ultrasonic wave.

When an ultrasonic wave reaches a reflection source, the phenomena of reflection, refraction and scattering occur at the reflection source. In the case where the ultrasonic wave is a longitudinal wave, a longitudinal wave and also a transverse wave are generated at the reflection source. Similarly, in the case where the ultrasonic wave is a transverse wave, a transverse wave and also a longitudinal wave are generated at the reflection source. This is the phenomenon called mode conversion.

The prior filed patent application (PCT/JP2004/16982) hypothesizes the existence of expression 5 shown below as a physical phenomenon by which the relationship shown by expression 4 holds, as described below in detail.

$$\frac{f_{s1}}{f_1} = \frac{V_S}{V_P} \qquad \text{[Expression 5]}$$

On the other hand, according to an existent universal ultrasonic theory, when the mode conversion described above (a phenomenon that the longitudinal wave is converted into a transverse wave and a transverse wave is converted into a longitudinal wave) occurs, the speed of the ultrasonic wave changes but the frequency does not change. According to this conventional theory, the existence of expressions 4 and 5 is denied.

As described below in detail, the ultrasonic inspection method in this embodiment is an analysis method which adopts, as truth, both the physical phenomenon shown by expressions 4 and 5 and the conventional ultrasonic theory that when the mode conversion occurs, the speed of the ultrasonic wave changes before and after the conversion but the frequency does not change.

Hereinafter, this analysis method will be described.

This analysis method uses sizing coefficients ($n_{s1}$, $n_{s2}$, $n_{s3}$, $n_{s4}$) in order to improve the precision of the sizing of the flaw Z which is to be inspected.

Here, $n_{s1}$ and $n_{s3}$ are real numbers of 1.0 or greater, and $n_{s2}$ and $n_{s4}$ are integers of 1 or greater.

The sizing coefficient $n_{s1}$ will be specifically described below.

As described above, the wave as an analysis target (i.e., component wave) is labeled as $GA_j(t)$ (j is the measurement point number), and the component wave $GA_j(t)$ is created using expressions 8 and 9 which will be described later in the section in which $n_{s4}$ is explained. In a comparative display of the component waves $GA_j(t)$ in accordance with j (=1 through $n_A$; $n_A$ is the number of measurement points), the maximum amplitude at each component wave $GA_j(t)$ is labeled as $A_j$, and the maximum value among the amplitudes $A_j$ is labeled as $A_{max}$. Then, the sizing coefficient $n_{s1}$ is defined.

Using the sizing coefficient $n_{s1}$, $GA_j(t)$ which fulfills $A_j \geq (1/n_{s1})A_{max}$ is replaced with the value of $(A_{max}/A_j)GA_j(t)$, and a $\tilde{GA}_j(t)$ wave found by expression 6 is created. ("G" represents a code having "~" above G as shown in the expressions; this is applied hereinafter.)

$$\tilde{GA}_j(t) = (1/A_{max})GA_j(t) \qquad \text{[Expression 6]}$$

After this, as shown in expression 7, the $GA_j(t)$ wave is replaced with the $\tilde{GA}_j(t)$ wave.

$$GA_j(t) \leftarrow \tilde{GA}_j(t) \qquad \text{[Expression 7]}$$

The sizing coefficient $n_{s1}$ is a coefficient for the above-described processing.

The sizing coefficient $n_{s2}$ will be described below.

In the comparative display of the component waves $GA_j(t)$, the coefficient $n_{s2}$ is defined. A comparative display of $GA_j^{ns2}(t)$ is presented. Then, the amplitude difference among the component waves $GA_j(t)$ having different values of j (j=1 through $n_A$) becomes clear. The sizing coefficient $n_{s2}$ is for clarifying the amplitude difference.

The sizing coefficient $n_{s3}$ will be described below.

In the comparative display of $GA_j^{ns2}(t)$, the coefficient $n_{s3}$ is defined. A comparative display of $n_{s3} \cdot GA_j^{ns2}(t)$ is presented in order to clarify the amplitude difference among the $GA_j(t)$ waves having different values of j (j=1 through $n_A$). The sizing coefficient $n_{s3}$ is for realizing this comparison.

The sizing coefficient $n_{s4}$ will be described below.

By performing Fourier transformation of the received origin wave (so-called received wave) $G_j(t)$, a spectrum $F_j(f)$ as shown in FIG. 9(a) is found. Using one method for extracting the spectrum at the $f_0$ position on the horizontal axis ($f_0$ is the central frequency for spectrum extraction), an arbitrary function $S(f)$ shown in FIG. 9(a) is multiplied by the function $F_j(f)$. As a result, a narrowband spectrum $FA_j(f)$ as shown in expression 8 and FIG. 9(b) is obtained.

$$FA_j(f) = S(f)^{ns4} \cdot F_j(f) \qquad \text{[Expression 8]}$$

The sizing coefficient $n_{s4}$ is an integer of 1 or greater. When the value of $n_{s4}$ is increased, the bandwidth of the $FA_j(f)$ spectrum (narrowband spectrum) obtained by the computation of expression 8 can be decreased.

The function $S(f)$ is a frequency function which:
has an increasing function of f=0 through $f_0$;
is 1.0 when $f=f_0$;
has a decreasing function of $f=f_0$ through $2f_0$; and
is 0.0 when $f \geq 2f_0$.

The analysis in this embodiment is performed as follows. The narrowband spectrum $FA_j(f)$ is obtained by expression 8 using the sizing coefficient $n_{s4}$. By Fourier transformation (expression 9) of the narrowband spectrum $FA_j(f)$, the component wave $GA_j(t)$ is obtained. The component wave $GA_j(t)$ is corrected (expressions 6 and 7) using the sizing coefficient $n_{s1}$ as described in the explanation of $n_{s1}$. From the corrected component wave $GA_j(t)$, $n_{s3} \cdot GA_j^{ns2}(t)$ is created using the sizing coefficients $n_{s2}$ and $n_{s3}$. A comparative display of $n_{s3} \cdot GA_j^{ns2}(t)$ is presented where the horizontal (or vertical) axis represents j (=1 through $n_A$) and the vertical (or horizontal) axis represents t. It is checked at each measurement point whether there is a wave generation correlating to the presence of the flaw Z in the cross-section perpendicular to the axis of the pipe.

$$GA_j(t) = \int_{-\infty}^{\infty} (FA_j(f) \cdot e^{i\omega t}) df \qquad \text{[Expression 9]}$$

Example 1

Now, the following analysis will be performed based on the above-described relational expressions. The longitudinal wave sonic speed of the SUS material used here is found to be 5 mm/μsec by the analysis of the receive wave $G_j(t)$ as described later.

The resonant frequency $f_1$ of the longitudinal wave which depends on the thickness (11 mm) of the pipe is represented as follows by expression 3.

$$f_1 = 10^6/(2 \times 1 \div 5) \approx 227 \text{ KHz} \qquad \text{[Expression 10]}$$

The resonant frequency $f_{s1}$ of the transverse wave which corresponds to $f_1$ and is generated under the hypothesis of expression 5 can be obtained by applying the sonic speed ratio of the transverse wave and the longitudinal wave of the SUS material, i.e., $\gamma_1 = 0.54$, to expression 4.

$$f_{s1} = 0.54 \, f_1 = 0.54 \times 227 \approx 122.5 \text{ KHz} \qquad \text{[Expression 11]}$$

Figure 10:
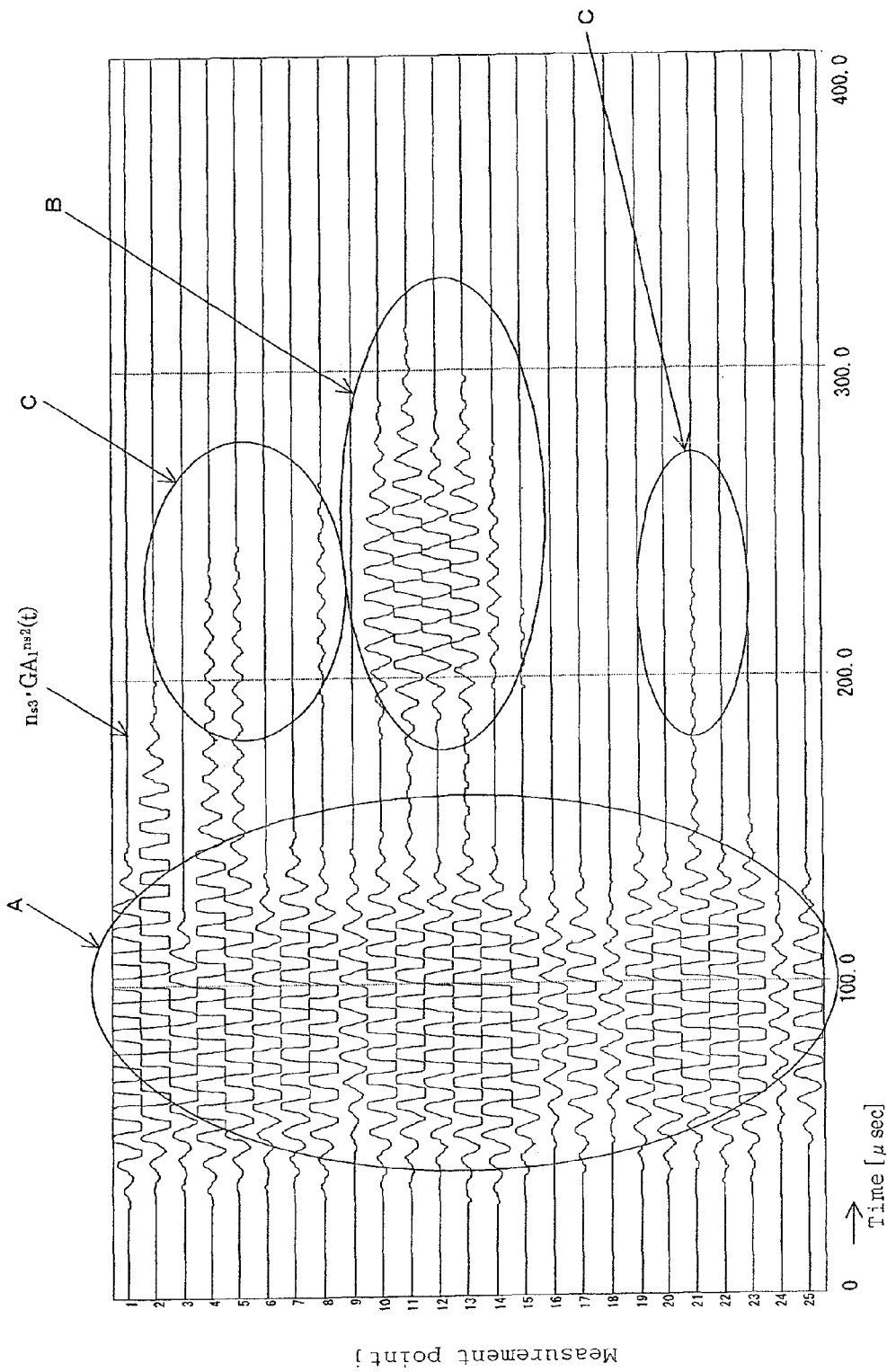
FIG. 10 is a chart comparing component waves.

FIG. 10 shows an example of analysis result obtained with the values of the sizing coefficients being $n_{s1}=1$, $n_{s2}=4$, $n_{s3}=9$ and $n_{s4}=200$. Hereinafter, a specific method for extracting the analyzed wave shown in FIG. 10 will be described.

The transverse wave primary resonant frequency which has a relationship with the above-mentioned thickness, i.e., $f_{S1}=122.5$ kHz, is labeled as $f_0$. $\Delta f_0 = 2.5$ kHz is defined as an appropriate value by an external instruction. An initial value $f_{ST}$ of the extraction frequency of a very narrowband wave is set to be $f_{ST} = f_0 - \Delta f_0 = 120$ kHz. The narrowband spectrum $FA_j(f)$ is calculated using expression 8, which is defined using the spectrum $F_j(f)$ corresponding to the received wave $G_j(t)$.

The function $S(f)$, which is described above in detail immediately below expression 8, will be described again. $S(f)$ is a frequency function which:
has an increasing function of f=0 through $f_{ST}$;
is 1.0 when $f=f_{ST}$;
has a decreasing function of $f=f_{ST}$ through $2f_{ST}$; and
is 0.0 when $f \geq 2f_{ST}$.
In this analysis, the increasing function and the decreasing function are sine and cosine functions.

The time series wave (component wave) $G_j(t)$ which corresponds to the narrowband spectrum $FA_j(f)$ is calculated using the inverse Fourier transformation (expression 9). Where the maximum amplitude at each component wave $GA_j(t)$ is $A_j$ and the maximum value among the amplitudes $A_j$ is $A_{max}$, the component wave $GA_j(t)$ which fulfills $A_j \geq (1/n_{s1})A_{max}$ is replaced with $(A_{max}/A_j)GA_j(t)$, and the $\tilde{GA}_j(t)$ wave calculated by expression 6 is created.

After this, as shown in expression 7, the component wave $GA_j(t)$ is replaced with the $GA_j(t)$ wave.

The analysis result in a comparative display of FIG. 10 is obtained by calculating $n_{s3} \cdot GA_j^{ns2}$ using $n_{s2}$ and $n_{s3}$. In FIG. 10, the waves in area A propagate in the thickness of the pipe along the interval $a_2$ between the pair of probes 31 and 32 in FIG. 6. The waves in area B are generated in correlation with the presence of the flaw Z and propagate in the thickness of the pipe. The waves in area C are tiny inspection disturbing waves.

The analysis of FIG. 10 is performed where the initial value of the extraction frequency of the very narrowband wave is $f_{ST}$=120 kHz. According to one method for reducing the generation of the inspection disturbing waves in area C in FIG. 10 to a minimum possible level, the above-described processing is repeated with the value of $f_{ST}$ being sequentially changed. Thus, the waves in area B in FIG. 10 which correlate to the presence of the flaw Z can be more clearly extracted.

With $\Delta f_{ST}$=0.5 kHz (may be externally specified or a predefined constant), expression 12 is obtained.

$$f_{ST} \leftarrow f_{ST} + \Delta f_{ST} \qquad \text{[Expression 12]}$$

Each time when the processing of expression 12 is performed, the component wave $GA_j(t)$ is re-calculated using expressions 8 and 9 successively. Thus, the component wave $GA_j(t)$ is corrected by the method described above for explaining the sizing coefficient $n_{s1}$ (using the expressions 6 and 7), and a comparative display of $n_{s3} \cdot GA_j^{ns2}$ is presented. Then, the generation of the waves in area B in FIG. 10 can be visually recognized more clearly.

Figure 11:
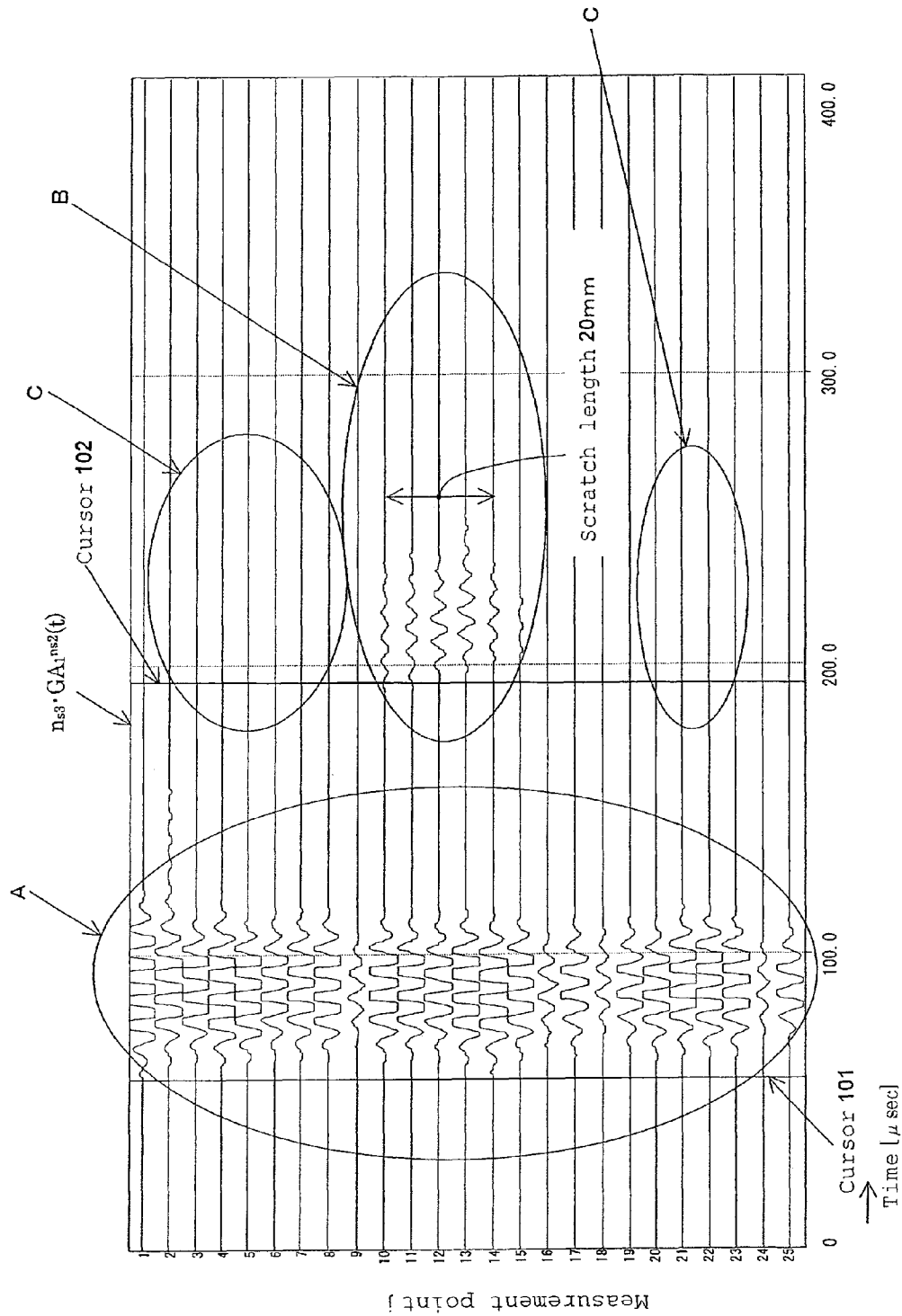
FIG. 11 is a chart comparing component waves.

FIG. 11 shows an analysis result obtained during this visual recognition when $f_{ST}$=122 kHz. In FIG. 11, the generation of the disturbing waves in area C is reduced, and the generation of the waves in area B which correlates to the presence of the flaw Z can be clearly recognized. The values of the sizing coefficients used when the result of FIG. 11 is obtained are $n_{s1}$=1, $n_{s2}$=4, $n_{s3}$=5 and $n_{s4}$=50.

The above-described analysis (which obtains the comparative displays in FIG. 10 and FIG. 11) is performed where the longitudinal wave sonic speed $V_P$ of the pipe is 5 mm/μsec. It is understood that the longitudinal wave sonic speed of a steel material is generally 5.9 mm/μsec, and that the longitudinal wave sonic speed of an SUS material is generally 5.7 mm/μsec.

In this analysis, the received wave $G_j(t)$ in the above-described pipe model is analyzed without using the generally known SUS material having the above-mentioned sonic speed.

Figure 12:
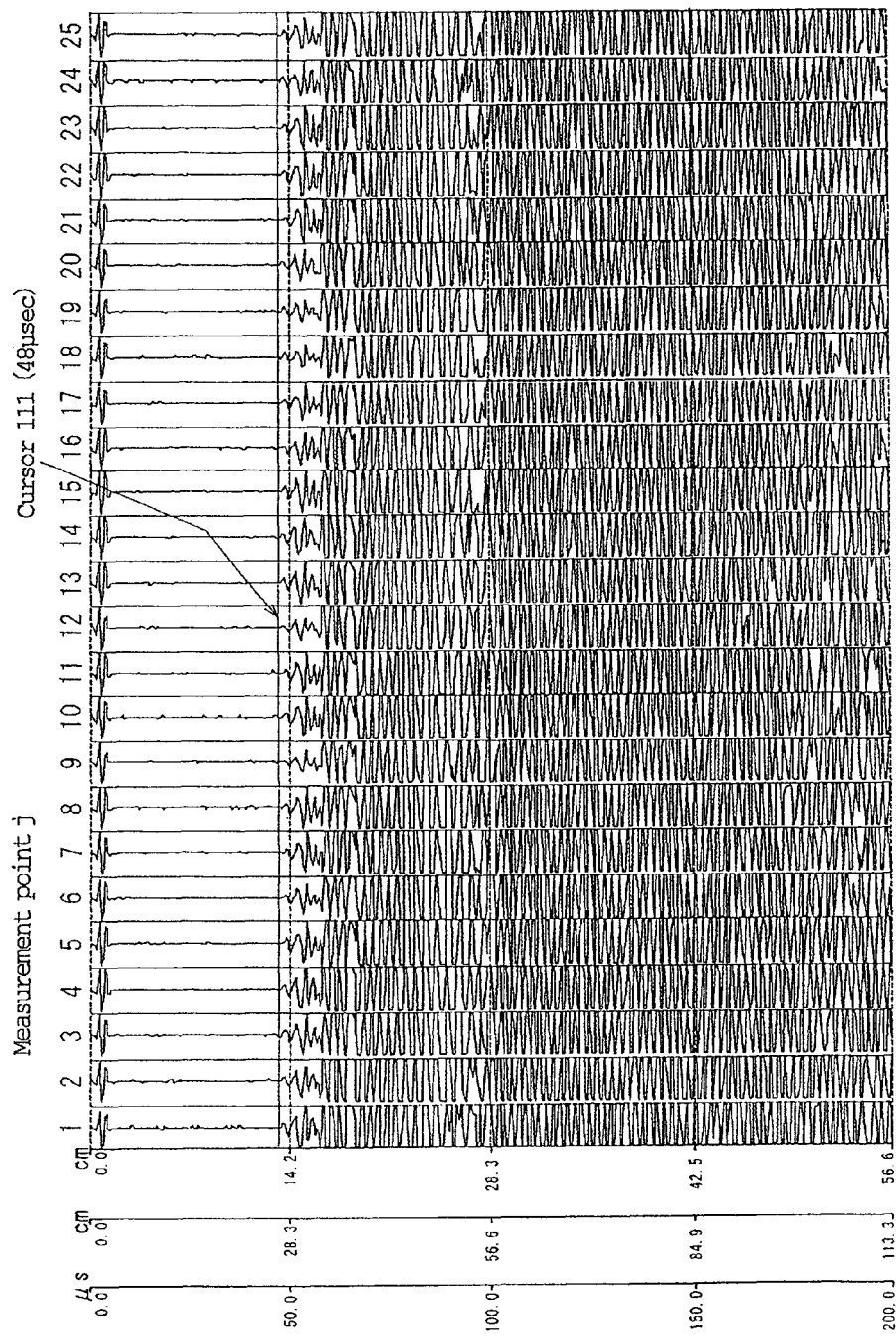
FIG. 12 is a comparative chart showing the generation time of a longitudinal wave.

Even for a naturally occurring longitudinal wave in a circumferential direction having a tiny amplitude, the time of generation can be accurately found. FIG. 12 is a comparative display of the component wave $GA_j(t)$ found by expressions 8 and 9 with $f_{ST}$=500 kHz and $n_{s4}$=3, using the sizing coefficients $n_{s1}$=1, $n_{s2}$=1 and $n_{s3}$=50. Because the amplitude is displayed 50 times larger by $n_{s3}$=50, the position of generation of the tiny longitudinal wave which propagates in an arc along the interval $a_2$ between the pair of probes 31 and 32 is specified by a cursor 111 (48.0 μsec) in FIG. 12.

The longitudinal wave sonic speed $V_P$ is calculated as below where the diameter of the oscillator is $\phi$=10 mm as described above.

$$V_P = (a_2 - \phi)/48.0 = (250 \text{ mm} - 10 \text{ mm})/48.0 = 5.0 \text{ mm/μsec} \qquad \text{[Expression 13]}$$

An examination of the analysis result of FIG. 11 finds that the time of generation of the wave first generated is indicated by a cursor 101 (about 50 μsec). The waves which correlate to the presence of the flaw Z are generated at measurement points 10 through 14 (length 4×$\Delta L$=4×5 mm=20 mm) (see area B). The time of generation thereof is indicated by a cursor 102 (about 174.8 μsec).

Using the longitudinal wave sonic speed $V_P$=5 mm/μsec, the length $b_2$ is calculated as follows based on the interval $a_2$ between the pair of probes 31 and 32 and the measurement position of the flaw Z.

1) Distance $a_2$ between the probes $$a_2 = 50 \text{ μsec} \times 5 \text{ mm/μsec} = 250 \text{ mm} \qquad \text{[Expression 14]}$$

(actual value: 250 mm)

2) Position of the flaw

Assuming that a wave generated from the position of the cursor 102 is a wave $B_1$ reflected by the flaw Z shown in FIG. 6, the position of the flaw is defined as follows.

$$b_2 = (174.8 \text{ μsec} \times 5 \text{ mm/μsec})/2 = 437 \text{ mm} \qquad \text{[Expression 15]}$$

(actual value: 437.5 mm)

An important phenomenon generated in this analysis will be described. The comparative displays of FIG. 10 and FIG. 11 are obtained with the hypothesis that expressions 4 and 5 hold.

In the comparative views of FIG. 10 and FIG. 11, the very narrowband component waves at the frequency of $n_c \cdot f_{s1}$ are shown with $n_c$ being 1 and using the transverse wave resonant frequency $f_{s1}$ ($=(V_S/V_P) \cdot f_1$) having a relationship with the thickness of the pipe and also using the sizing coefficients $n_{s1}$ through $n_{s4}$. When a component wave is extracted at the transverse wave resonant frequency, the extracted wave should be a transverse wave. However, the distance $a_2$ between the probes shown by expression 14 and the value of $b_2$ representing the flaw position shown by expression 15 are accurately specified at the longitudinal wave sonic speed $V_P$=5 mm/μsec.

From this, the extracted waves in FIG. 10 and FIG. 11 should be determined to be longitudinal waves. The conclusion is that the extracted waves in FIG. 10 and FIG. 11 are longitudinal waves.

The reason for this will be described, hereinafter.

As described above, there are two pieces of truth in the physical phenomena of reflection, refraction and mode conversion of an ultrasonic wave.

A first piece of truth is the following.

According to the conventional ultrasonic theory, when the mode conversion occurs along with the reflection or refraction, the sonic speed of the wave changes before and after the conversion but the frequency does not change (truth (1)).

A second piece of truth is the following.

When the mode conversion from a longitudinal wave into a transverse wave occurs or when the mode conversion from a transverse wave into a longitudinal wave occurs, the waves generated by the mode conversion include a wave having the same frequency as that of the pre-mode conversion wave as shown by truth (1) as well as a wave having a frequency defined by expression 5 (truth (2)).

The extracted waves in FIG. 10 and FIG. 11 are longitudinal waves as a result of the two pieces of truth being associated with each other.

A longitudinal wave which is input from the circumferential surface of the pipe toward the center of the cross-section of the pipe is repeatedly mode-converted under the relationship of expression 5 of truth (2), each time when the wave is multiple-reflected by the thickness of the pipe. When the transverse wave generated by the mode conversion is converted into a longitudinal wave, there occur the conversion based on expression 5 and also the conversion of truth (1) without the frequency being changed (the conventional ultrasonic theory).

Because of this, a longitudinal wave, having the frequency $f_{S1}$ of the transverse wave obtained by expression 5, appears.

This is the reason why the waves which correlate to the flaw Z in area B in FIG. 10 and FIG. 11 are longitudinal waves.

Figure 9:
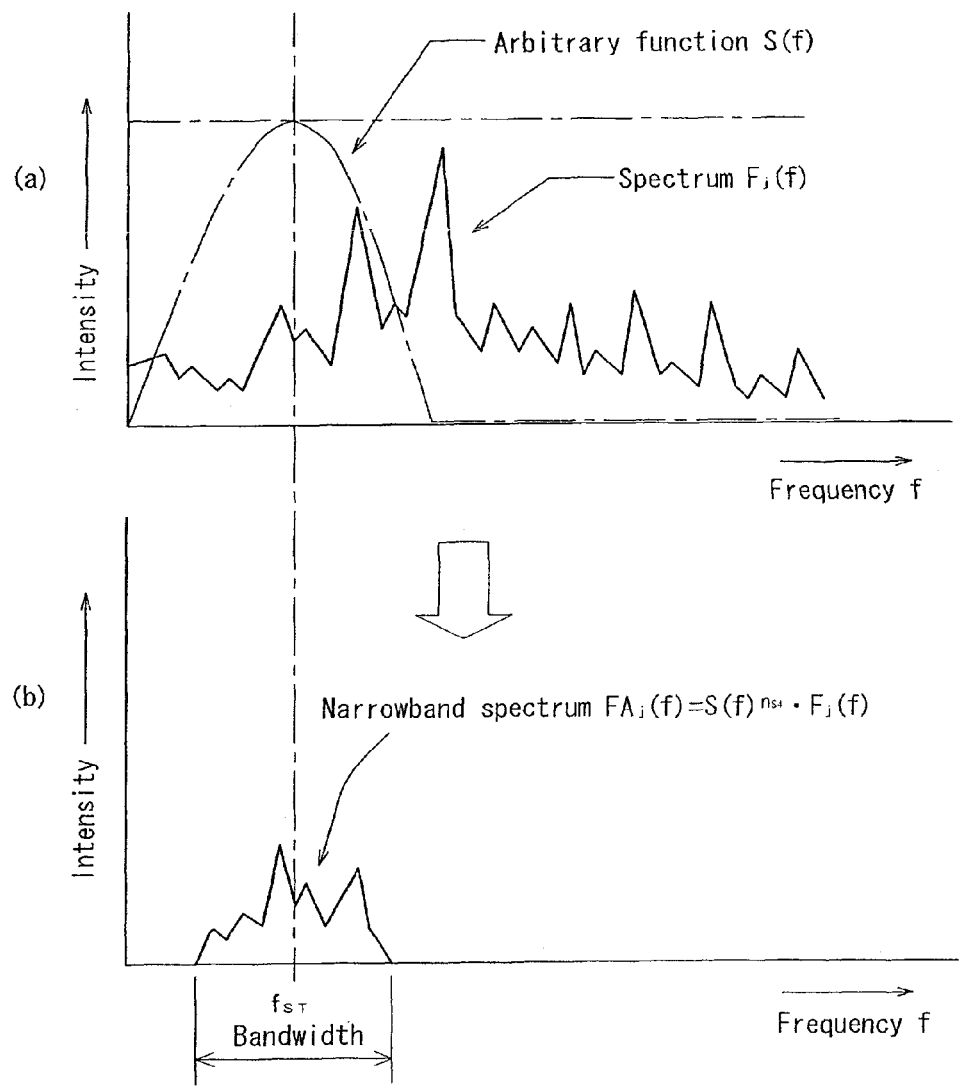
FIG. 9 shows graphs illustrating extractions of a narrowband spectrum.

The analysis results shown in FIG. 10 and FIG. 11 are obtained using the frequency function S(f) used in expression 8. Even where S(f) is replaced with a function which is:

0.0 when $0 \leq f < f_{ST} - \Delta f$;

1.0 when $f_{ST} - \Delta f \leq f \leq f_{ST} + \Delta f$; and 0.0 when $f_{ST} + \Delta f < f$ using a predefined or externally given Δf value (a real number of 0 or greater), almost the same analysis results (not shown) as those of FIG. 10 and FIG. 11 are obtained as long as the value of Δf is set to be about ½ of the bandwidth (see FIG. 9(*b*)) of $S(f)^{ns4} \cdot F(f)$ used in the analysis which results in FIG. 10 and FIG. 11.

As described above, the following various effects are obtained by performing inspection by the ultrasonic inspection method in Example 1.

Figure 13:
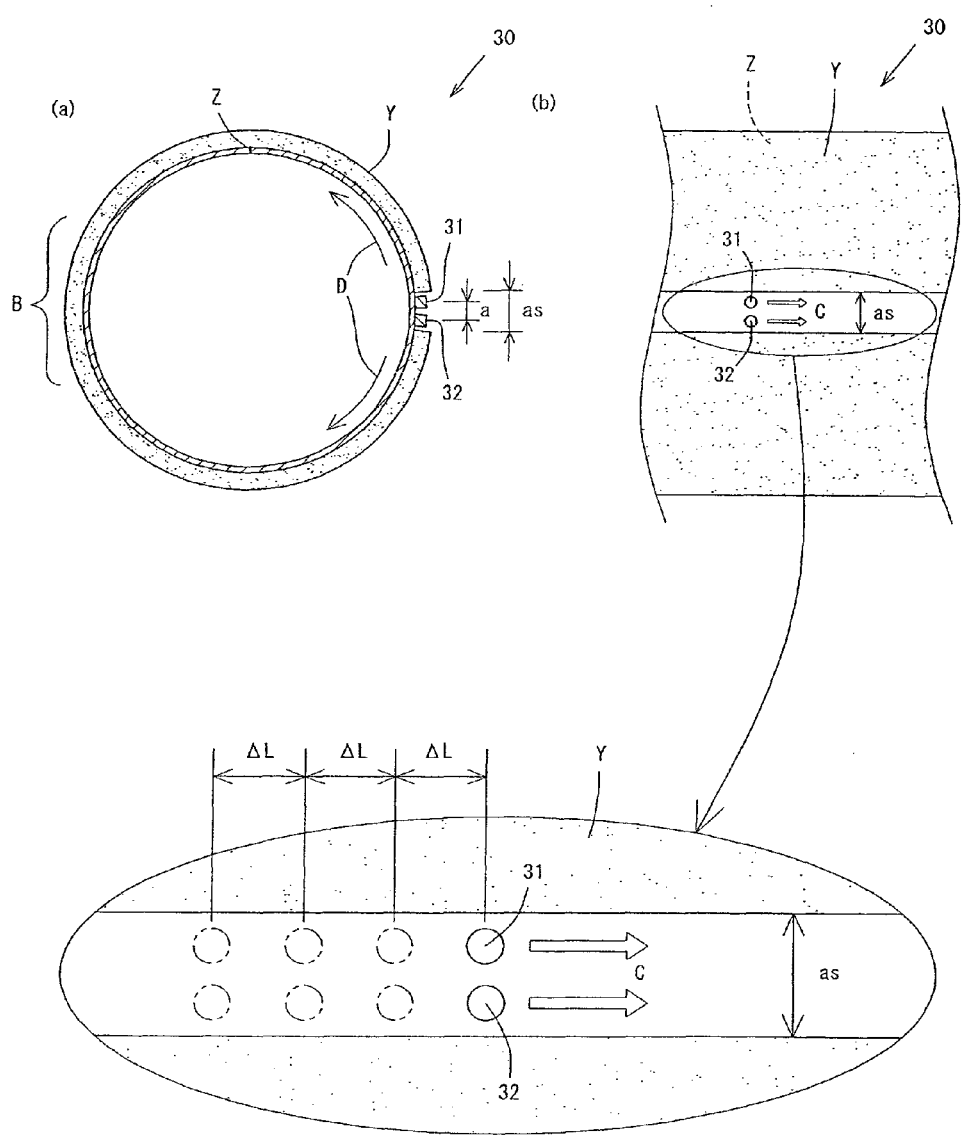
FIG. 13 shows illustrations of a measurement by which the probes provided at a set positions are moved in the axial direction of the pipe.

For example, in the case where the measurement target is the inspection target 30 which is a pipe covered with a protective member around an outer circumference thereof, the measurement can proceed by the above-described measurement method by, as shown in FIGS. 13(*a*) and (*b*), setting a probe provision area, having a width $a_s$ and extending in the axial direction of the pipe, at a position in the circumferential direction of the pipe.

Namely, referring to FIGS. 13(*a*) and (*b*), the transmission probe 31 and the reception probe 32 are located at positions where the protective member Y is not provided, the line segment connecting the transmission probe 31 and the reception probe 32 is on the pipe surface on the cross-section perpendicular to the axis of the pipe, and the interval between the probes is labeled as "a". Each time when the pair of probes are moved in the axial direction of the pipe by ΔL while the interval therebetween is maintained at "a", a wideband received wave $G_j(t)$ (j=1 through $n_A$; $n_A$ is the number of measurement points) is obtained. Thus, the measurement can proceed in the same manner as described above. As understood from this, according to the above-described measurement method, even where the pipe is covered with the protective member Y or where the measurement at position B shown in FIG. 13(*a*) is difficult or impossible by the conventional ultrasonic method due to the setting conditions of the pipe, the flaw can be inspected by performing a measurement at a position opposite to position B.

According to the conventional ultrasonic method, the measurement needs to be performed where the pair of probes 31 and 32 are sequentially moved in the axial direction of the pipe (direction C) as well as in the circumferential direction of the cross-section of the pipe (direction D) while the interval "a" is maintained. Such a measurement requires a difficult work and a long time when the pipe has a large diameter. In the case where, for example, the pipe is provided with the protective member Y scattered on the surface thereof as shown in the figures, the conventional ultrasonic method requires the protective member to be removed and the pipe surface to be polished.

By contrast, the novel measurement shown in FIG. 13 by which the probes provided at a set position are moved in the axial direction of the pipe realizes the following. An area which has a width of $a_s$ and extends in the axial direction of the pipe is prepared as an area for providing the probes, and the protective member Y is not provided on this area. Then, the measurement time can be significantly reduced, and the steps of removing the protective member and polishing the surface of the pipe become unnecessary, unlike by the conventional ultrasonic method.

The number of the control coefficients required for an automatic measurement is significantly smaller than in the conventional ultrasonic method, and thus automatic control on the movement of the probes and the corresponding analysis processing become easier.

Namely, the main control coefficients for automation are:
 i) interval "a" between the probes,
 ii) initial positions of the probes,
 iii) moving direction C of the probes along the axis of the pipe,
 iv) moving value ΔL for making the probes discrete from the initial positions, and
 v) measurement range $n_A \cdot \Delta L$.

Example 2

In the above, an example of inspecting the flaw Z made in the thickness of the cross-section perpendicular to the axial direction of the cylindrical pipe and extending in the circumferential direction of the cross-section is described. According to an analysis method in Example 2, the method of locating and moving the pair of probes 31 and 32 is changed from that shown in FIGS. 6(*a*) and (*b*) or FIGS. 13(*a*) and (*b*) to that shown in FIGS. 14(*a*) and (*b*).

Figure 14:
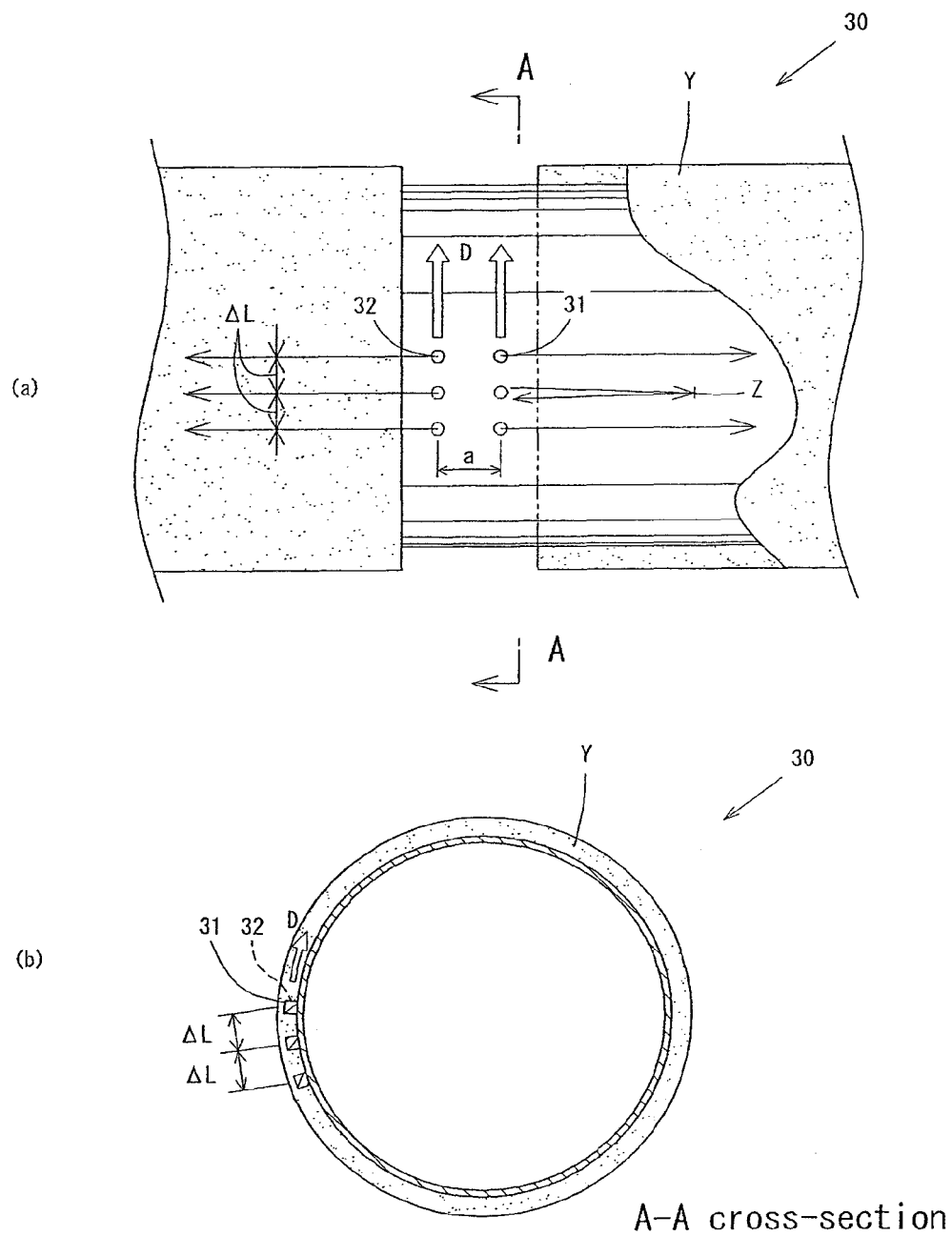
FIG. 14 shows illustrations of a measurement by which the probes provided at a set positions are moved in the axial direction of the pipe.
Figure 15:
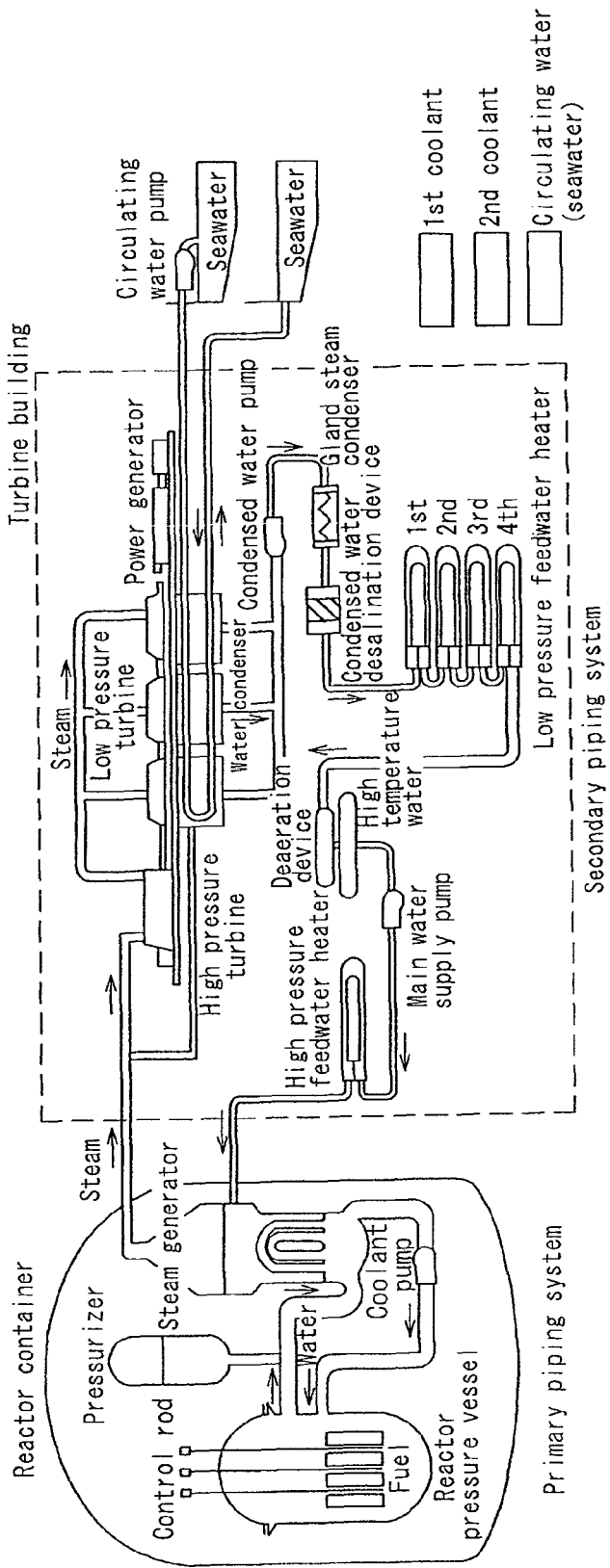
FIG. 15 is diagram illustrating a primary piping system and a secondary piping system.

FIG. 14 (*a*) illustrates the analysis method of Example 2, and FIG. 14(*b*) is a cross-sectional view taken along line A-A of the pipe shown in FIG. 14(*a*).

This analysis is performed as follows. The pair of probes are located such that the line segment connecting the centers of the probes is parallel to the axis of the pipe. The probes are moved on the pipe surface in the circumferential direction (direction D in FIG. 14) of the cross-section perpendicular to the axis of the pipe while the interval therebetween is maintained at "a". Each time when the probes are moved by ΔL, a $G_j(t)$ wave (j=1 through $n_A$) is obtained, and the $G_j(t)$ wave is analyzed by the analysis method shown in Example 1.

By such an analysis method, whether a flaw Z extending in the axial direction of the pipe is present in the thickness of the pipe, and the position of the flaw, can be inspected. Specific analysis examples are exactly the same as those in Example 1 and will not be shown here particularly.

Integer $n_c$ of 1 or greater in this embodiment corresponds to integer n of 1 or greater in the present invention. However, the present invention is not limited to the structure of the above-described embodiment and may be carried out in various embodiments as described above.

INDUSTRIAL APPLICABILITY

The present invention is applicable for inspecting flaws inside an inspection target such as a pipe formed of stainless steel, inconel, cast iron or other metal materials or a structure built by, for example, a construction or civil engineering work.

The invention claimed is:
1. An ultrasonic inspection method utilizing a resonance phenomenon of continuously transmitting a wideband ultrasonic wave by a transmission probe and receiving a wideband ultrasonic wave from an inspection target by a reception probe, wherein a measurement is performed with the transmission probe and the reception probe being located on a surface of a cylindrical pipe on a cross-section perpendicular to a direction along a cylindrical axis of the pipe, where the length of a curve connecting the centers of the pair of probes is labeled as "a" and the curve is matched to an arc of the cross-section;

the method comprising:

executing a first step of transmitting a wideband ultrasonic wave from the transmission probe toward the central point of the cross-section of the cylindrical pipe perpendicular to the direction along to the cylindrical axis of the pipe by an externally specified number of times ($n_B$); receiving a wideband received wave by the reception probe each time when the transmission is performed; and adding the $n_B$ number of the wideband received waves $G_1(t)$ obtained in accordance with the specified number of times at a position of the receipt and averaging the addition result with a time area;

executing the first step each time when the pair of probes are translated in the direction along the cylindrical axis of the pipe by a predefined or externally given predetermined value $\Delta L$ while the pair of probes are kept as distanced by the interval "a"; and executing a second step of performing the first step by an externally given predetermined number of times $n_A$ and thus obtaining all the wideband received waves $G_j(t)$ (j=1 through $n_A$);

executing a third step of calculating a longitudinal primary resonant frequency $f_1$ which has a relationship with a thickness of the inspection target by:

$$f_1 = 10^6/(2W \div V_P) \quad \text{[Expression 16]}$$

where the thickness of the inspection target is W (mm), the longitudinal wave sonic speed is $V_P$ (mm/μsec) and the sonic speed ratio of a transverse wave and the longitudinal wave is $\gamma_1$, and calculating a primary resonant frequency $f_{S1}$ of the transverse wave generated by mode conversion by:

$$f_{s1} = \gamma_1 \cdot f_1 \quad \text{[Expression 17]}$$

and successively performing analyses of step 4, step 5 and step 6 shown below using sizing coefficients $n_{s1}$, $n_{s2}$, $n_{s3}$ and $n_{s4}$ for inspecting, at high precision, presence/absence of a flaw of the inspection target and time-wise development of the flaw, and using a comparative display of the obtained component waves $GA_j(t)$ to analyze the presence/absence of the flaw in the cross-section perpendicular to the direction along the cylindrical axis of the cylindrical pipe on which the transmission probe and the reception probe are located and to analyze a position of the flaw on a circumference surface of the pipe:

step 4: step by which GAO is processed by Fourier transformation to find $F_j(f)$, n is an integer of 1 or greater, $f_{ST} = n \cdot f_1$ or $f_{ST} = n \cdot f_{S1}$ is found to create an arbitrarily-defined frequency function S(f) which has an increasing function of f=0 through $f_{ST}$, is 1.0 when $f = f_{ST}$, has a decreasing function of $f = f_{ST}$ through $2f_{ST}$ and is 0.0 when $f \geq 2f_{ST}$, an $FA_j(t)$ function is found by:

$$FA_j(f) = S(f)^{ns4} \cdot F_j(f) \quad \text{[Expression 8]}$$

using the sizing coefficient $n_{s4}$, and the corresponding component wave $GA_j(t)$ is found by:

$$GA_j(t) = \int_{-\infty}^{\infty} (FA_j(f) \cdot e^{j\omega t}) df \quad \text{[Expression 9]}$$

step 5: step by which a maximum amplitude of each component wave $GA_j(t)$ (j=1 through $n_A$) obtained in step 4 is found and labeled as $A_j$, the maximum value among $A_j$ is labeled as $A_{max}$, the component wave $GA_j(t)$ which fulfills $A_j \geq (1/n_{s1})A_{max}$ is replaced with $(A_{max}/A_j)GA_j(t)$, a $GA_j(t)$ wave calculated by:

$$GA_j(t) = (1/A_{max})GA_j(t) \quad \text{[Expression 6]}$$

is created, and the component wave $GA_j(t)$ is replaced with $GA_j(t)$;

step 6: step by which an $n_{s3} \cdot GA_j^{ns2}(t)$ wave is created using the sizing coefficients $n_{s2}$ and $n_{s3}$, and the $GA_j(t)$ wave is replaced with the $n_{a3} \cdot GA_j^{ns2}(t)$ wave.

2. An ultrasonic inspection method utilizing a resonance phenomenon of continuously transmitting a wideband ultrasonic wave by a transmission probe and receiving a wideband ultrasonic wave from an inspection target by a reception probe, wherein a measurement is performed with the transmission probe and the reception probe being located on a surface of a cylindrical pipe on a cross-section perpendicular to a direction along a cylindrical axis of the pipe, where the length of a line segment connecting the centers of the pair of probes is labeled as "a" and the line segment is matched to the direction along the cylindrical axis of the cylindrical pipe;

the method comprising:

executing a first step of transmitting a wideband ultrasonic wave from the transmission probe toward the central point of the cross-section of the cylindrical pipe by an externally specified number of times ($n_B$); receiving a wideband received wave by the reception probe each time when the transmission is performed; and adding the $n_B$ number of the wideband received waves $G_1(t)$ obtained in accordance with the specified number of times at a position of the receipt and averaging the addition result with a time area;

executing the first step each time when the line segment connecting the pair of probes is translated with respect to the direction along the cylindrical axis of the pipe on the surface of the pipe on the cross-section perpendicular to the axis of the pipe by a predefined or externally given predetermined value $\Delta L$ while the pair of probes are kept as distanced by the interval "a"; and executing a second step of performing the first step by an externally given predetermined number of times $n_A$ and thus obtaining all the wideband received waves $G_j(t)$ (j=1 through $n_A$);

executing a third step of calculating a longitudinal primary resonant frequency $f_1$ which has a relationship with a thickness of the inspection target by:

$$f_1 = 10^6/(2W \div V_P) \quad \text{[Expression 16]}$$

where the thickness of the inspection target is W (mm), the longitudinal wave sonic speed is $V_P$ (mm/gsec) and the sonic speed ratio of a transverse wave and the longitudinal wave is $\gamma_1$, and calculating a primary resonant frequency $f_{S1}$ of the transverse wave generated by mode conversion by:

$$f_{s1} = \gamma_1 \cdot f_1 \quad \text{[Expression 17]}$$

and successively performing analyses of step 4, step 5 and step 6 shown below using sizing coefficients $n_{s1}$, $n_{s2}$, $n_{s3}$ and $n_{s4}$ for inspecting, at high precision, presence/absence of a flaw of the inspection target and time-wise development of the flaw, and using a comparative display of the obtained component waves $GA_j(t)$ to analyze the presence/absence of the flaw in a thickness in a radial direction of the cross-section of the pipe on a line extended from the line segment connecting the centers of the transmission probe and the reception probe and to analyze a position of the flaw in the direction along the cylindrical axis of the pipe:

step 4: step by which $G_j(t)$ is processed by Fourier transformation to find $F_j(f)$, n is an integer of 1 or greater, $f_{ST}=n \cdot f_1$ or $f_{ST}=n \cdot f_{S1}$ is found to create an arbitrarily-defined frequency function S(f) which has an increasing function of f=0 through $f_{ST}$, is 1.0 when f=$f_{ST}$, has a decreasing function of f=$f_{ST}$ through $2f_{ST}$ and is 0.0 when f≧$2f_{ST}$, an $FA_j(t)$ function is found by:

$$FA_j(f)=S(f)^{s4} \cdot F_j(f) \quad \text{[Expression 8]}$$

using the sizing coefficient $n_{s4}$, and the corresponding component wave $GA_j(t)$ is found by:

$$GA_j(t) = \int_{-\infty}^{\infty} (FA_j(f) \cdot e^{i\omega t}) df \quad \text{[Expression 9]}$$

step 5: step by which a maximum amplitude of each component wave $GA_j(t)$ (j=1 through $n_A$) obtained in step 4 is found and labeled as $A_j$, the maximum value among $A_j$ is labeled as $A_{max}$, the component wave $GA_j(t)$ which fulfills $A_j≧(1/n_{s1})A_{max}$ is replaced with $(A_{max}/A_j)GA_j(t)$, a $GA_j(t)$ wave calculated by:

$$GA_j(t)=(1/A_{max})GA_j(t) \quad \text{[Expression 6]}$$

is created, and the component wave $GA_j(t)$ is replaced with $GA_j(t)$;

step 6: step by which an $n_{s3} \cdot GA_j^{ns2}(t)$ wave is created using the sizing coefficients $n_{s2}$ and $n_{s3}$, and the $GA_j(t)$ wave is replaced with the $n_{s3} \cdot GA_j^{ns2}(t)$ wave.

3. An ultrasonic inspection method according to claim 1, wherein:

the processing of expression 4 is executed by processing, by which $G_j(t)$ is processed by Fourier transformation to find $F_j(f)$, n is an integer of 1 or greater, $f_{ST}=n \cdot f_1$ or $f_{ST}=n \cdot f_{S1}$ is found to create an arbitrarily-defined frequency function S(f) which is:

0.0 when $0≦f<f_{ST}-\Delta f$, 1.0 when $f_{ST}-\Delta f≦f≦f_{ST}+\Delta f$, and 0.0 when $f_{ST}+\Delta f<f$ using a predetermined value $\Delta f$ (predefined or externally given value), and an $FA_j(f)$ function is found by:

$$FA_j(f)=S(f)^{ns4} \cdot F_j(f) \quad \text{[Expression 8]}$$

using the sizing coefficient $n_{s4}$, and the corresponding $GA_j(t)$ wave is found by:

$$GA_j(t) = \int_{-\infty}^{\infty} (FA_j(f) \cdot e^{i\omega t}) df. \quad \text{[Expression 9]}$$

4. An ultrasonic inspection method according to claim 1, comprising a step by which $\Delta f_0$ (a real number of 0 or greater) is given by an external instruction, an initial value of $f_{ST}$ is made $f_{ST} \leftarrow f_{ST}-\Delta f_0$, each time when the processing of $f_{ST} \leftarrow f_{ST}+\Delta f_{ST}$ is executed using $\Delta f_{ST}$ (a real number of 0.0 or greater which is predefined or externally instructed), the analyses of step 4, step 5 and step 6 are successively performed, a comparative display of the obtained $GA_j(t)$ waves is presented, and the analyses of step 4, step 5 and step 6 can be stopped by an external instruction.

5. An ultrasonic inspection method according to claim 2, wherein:

the processing of expression 4 is executed by processing, by which $G_j(t)$ is processed by Fourier transformation to find $F_j(f)$, n is an integer of 1 or greater, $f_{ST}=n \cdot f_1$ or $f_{ST}=n \cdot f_{S1}$ is found to create an arbitrarily-defined frequency function S(f) which is:

0.0 when $0≦f<f_{ST}-\Delta f$, 1.0 when $f_{ST}-\Delta f≦f≦f_{ST}+\Delta f$, and 0.0 when $f_{ST}+\Delta f<f$ using a predetermined value $\Delta f$ (predefined or externally given value), and an $FA_j(f)$ function is found by:

$$FA_j(f)=S(f)^{ns4} \cdot F_j(f) \quad \text{[Expression 8]}$$

using the sizing coefficient $n_{s4}$, and the corresponding $GA_j(t)$ wave is found by:

$$GA_j(t) = \int_{-\infty}^{\infty} (FA_j(f) \cdot e^{i\omega t}) df. \quad \text{[Expression 9]}$$

6. An ultrasonic inspection method according to claim 2, comprising a step by which $\Delta f_0$ (a real number of 0 or greater) is given by an external instruction, an initial value of $f_{ST}$ is made $f_{ST} \leftarrow f_{ST}-\Delta f_0$, each time when the processing of $f_{ST} \leftarrow f_{ST}+\Delta f_{ST}$ is executed using $\Delta f_{ST}$ (a real number of 0.0 or greater which is predefined or externally instructed), the analyses of step 4, step 5 and step 6 are successively performed, a comparative display of the obtained $GA_j(t)$ waves is presented, and the analyses of step 4, step 5 and step 6 can be stopped by an external instruction.

7. An ultrasonic inspection method according to claim 3, comprising a step by which $\Delta f_0$ (a real number of 0 or greater) is given by an external instruction, an initial value of $f_{ST}$ is made $f_{ST} \leftarrow f_{ST}-\Delta f_0$, each time when the processing of $f_{ST} \leftarrow f_{ST}+\Delta f_{ST}$ is executed using $\Delta f_{ST}$ (a real number of 0.0 or greater which is predefined or externally instructed), the analyses of step 4, step 5 and step 6 are successively performed, a comparative display of the obtained $GA_j(t)$ waves is presented, and the analyses of step 4, step 5 and step 6 can be stopped by an external instruction.

8. An ultrasonic inspection method according to claim 4, comprising a step by which $\Delta f_0$ (a real number of 0 or greater) is given by an external instruction, an initial value of $f_{ST}$ is made $f_{ST} \leftarrow f_{ST}-\Delta f_0$, each time when the processing of $f_{ST} \leftarrow f_{ST}+\Delta f_{ST}$ is executed using $\Delta f_{ST}$ (a real number of 0.0 or greater which is predefined or externally instructed), the analyses of step 4, step 5 and step 6 are successively performed, a comparative display of the obtained $GA_j(t)$ waves is presented, and the analyses of step 4, step 5 and step 6 can be stopped by an external instruction.

9. An ultrasonic inspection method according to claim 5, comprising a step by which $\Delta f_0$ (a real number of 0 or greater) is given by an external instruction, an initial value of $f_{ST}$ is made $f_{ST} \leftarrow f_{ST} \Delta \Delta f_0$, each time when the processing of $f_{ST} \leftarrow f_{ST} + \Delta f_{ST}$ is executed using $\Delta f_{ST}$ (a real number of 0.0 or greater which is predefined or externally instructed), the analyses of step 4, step 5 and step 6 are successively performed, a comparative display of the obtained $GA_j(t)$ waves is presented, and the analyses of step 4, step 5 and step 6 can be stopped by an external instruction.

* * * * *